(12) United States Patent
Plowman et al.

(10) Patent No.: US 6,388,063 B1
(45) Date of Patent: May 14, 2002

(54) DIAGNOSIS AND TREATMENT OF SAD RELATED DISORDERS

(75) Inventors: Gregory D. Plowman, San Carlos, CA (US); Susan Onrust, Aukland (NZ); David Markby, San Francisco; Sara Courtneidge, Burlingame, both of CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/099,053

(22) Filed: Jun. 17, 1998

Related U.S. Application Data

(60) Provisional application No. 60/049,914, filed on Jun. 18, 1997.

(51) Int. Cl.[7] ............... C07H 21/04; C12N 5/16; C12N 15/09

(52) U.S. Cl. ............... 536/23.5; 536/24.3; 536/24.31; 435/69.1; 435/320.1; 435/325

(58) Field of Search ............... 536/23.1, 23.5, 536/24.3, 24.31, 69.1, 320.1, 325

(56) References Cited

U.S. PATENT DOCUMENTS

| | | |
|---|---|---|
| 4,343,940 A | 8/1982 | Kreighbaum et al. |
| 4,376,110 A | 3/1983 | David |
| 4,447,608 A | 5/1984 | Jones et al. |
| 4,757,072 A | 7/1988 | Kabbe et al. |
| 4,945,050 A | 7/1990 | Sandford et al. |
| 5,217,999 A | 6/1993 | Levitzki et al. |
| 5,283,173 A | 2/1994 | Fields et al. |
| 5,302,606 A | 4/1994 | Spada et al. |
| 5,316,553 A | 5/1994 | Kaul et al. |
| 5,330,992 A | 7/1994 | Eissenstat et al. |
| 5,336,615 A * | 8/1994 | Bell et al. ............ 435/240.2 |
| 5,610,173 A | 3/1997 | Schwartz et al. |

FOREIGN PATENT DOCUMENTS

| | | |
|---|---|---|
| EP | 0 562 734 | 9/1993 |
| EP | 0 566 226 | 10/1993 |
| EP | 0 520 722 | 12/1997 |
| WO | 91/15495 | 10/1991 |
| WO | 92/20642 | 11/1992 |
| WO | 92/21660 | 12/1992 |
| WO | 93/09236 | 5/1993 |
| WO | 93/10242 | 5/1993 |
| WO | 94/03427 | 2/1994 |
| WO | 94/14808 | 7/1994 |
| WO | 94/23039 | 10/1994 |
| WO | 95/06735 | 3/1995 |
| WO | 96/22976 | 8/1996 |
| WO | 96/94985 | 11/1996 |

OTHER PUBLICATIONS

New England Biolabs. 1993/94 Catalog, pp. 92–95.*
Abe et al., "Molecular Characterization of a Novel Metabotropic Glutamate Receptor mGluR5 Coupled to Inositol Pohosphate/$Ca^{2+}$ Signal," *J. Biol. Chem.* 267(19):13361–13368 (1992).
Altschul et al., "Basic Local Alignment Search Tool," *J. Mol. Biol.* 215:403–410 (1990).
Ausubel et al.(editor), *Current Protocols in Molecular Biology,* John Wiley & Sons (1994) (Table of Contents for vols. 1 & 2).
Barker et al., "In vitro activity of non–glutamate containing quinazoline–based thymidylate synthase inhibitors," *Proceedings of the American Association for Cancer Research* 32:327 at abstract No. 1939 (1991).
Bayer et al., "The Avidin–Biotin Complex in Affinity Cytochemistry," *Methods in Enzymology* 62:308–319 (1979).
Bendiak, "A Common Peptide Stretch Among Enzymes Localized to the Golgi Apparatus: Structural Similarity of Golgi–Associated Glycosyltransferases," *Biochemical and Biophysical Research Communications* 170:879–882 (1990).
Benoist and Chambon, "In vivo sequence requirements of the SV40 early promoter region," *Nature* 290:304–310 (1981).
Bertino, "Toward Improved Selectivity in Cancer Chemotherapy: The Richard and Hinda Rosenthal Foundation Award Lecture," *Cancer Research* 39:293–304 (1979).
Bolen, "Nonreceptor tyrosine protein kinases," *Oncogene* 8:2025–2031 (1993).
Bollon and Stauver, "DNA Transformation Efficiency of Various Bacterial and Yeast Host–Vector Systems," *Journal of Clinical Hematology and Oncology* 10(2&3):39–48 (1980).
Botstein et al., "Making mutations in vitro and Putting Them Back into Yeast," *Miami Winter Symposia—From Gene to Protein: Translation into Biotechnology,* edited by Ahmad et al., Academic Press, 19:265–274 (1982).
Broach, "The Yeast Plasmid $2\mu$ Circle," *Cell* 28:203–204 (1982).
Broach, "The Yeast Plasmid $2\mu$ Circle," in *The Molecular Biology of the Yeast Saccharomyces: Life Cycle and Inheritance,* Cold Spring Harbor Laboratory, Cold Spring Harbor, NY, pp. 445–470 (1981).

(List continued on next page.)

*Primary Examiner*—Anthony C. Caputa
*Assistant Examiner*—Anne L. Holleran
(74) *Attorney, Agent, or Firm*—Foley & Lardner

(57) ABSTRACT

The present invention relates to SAD polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for SAD related diseases or conditions characterized by an abnormal interaction between a SAD polypeptide and a SAD binding partner.

15 Claims, No Drawings

OTHER PUBLICATIONS

Brinster et al., "Factors Affecting the Efficiency of Introducing Foreign DNA into Mice by Microinjecting Eggs," *Proc. Natl. Acad. Sci. USA* 82:4438–4442 (1985).

Bullock et al., "Techniques in Immunocytochemistry," Academic Press, Orlando, FL: vol. 1 (1982), vol. 2 (1983), vol. 3 (1985) (Table of Contents Only).

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Protein–Tyrosine Kinase p56$^{lck\,1}$," *Journal of Medicinal Chemistry* 36(4):425–432 (1993).

Campbell, *Monoclonal Antibody Technology: Laboratory Techniques in Biochemistry and Molecular Biology*, vol. 13, Elsevier Science Publishers, Amsterdam, The Netherlands (1984) (Table of Contents Only).

Capecchi, "Altering the Genome by Homologous Recombination," *Science* 244:1288–1292 (1989).

Capecchi, "High Efficiency Transformation by Direct Microinjection of DNA into Cultured Mammalian Cells," *Cell* 22:479–488 (1980).

Cenatiempo, "Prokaryotic gene expression in vitro: transcription–translation coupled systems," *Biochimie* 68:505–515 (1986).

Chard, *An Introduction to Radioimmunoassay and Related Techniques*, Elsevier Science Publishers, Amsterdam, The Netherlands (1986) (Table of Contents Only).

Chater et al., "Streptomyces C31–Like Phages: Cloning Vectors, Genome Changes and Host Range," in *Sixth International Symposium on Actinomycetes Biology*, Akademiai Kaido, Budapest, Hungary, pp. 45–52 (1986).

Chen and Okayama, "High–Efficiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidinium Thiocyanate–Phenol–Chloroform Extraction," *Analytical Biochemistry* 162:156–159 (1987).

Chu et al., "Electroporation for the efficient transfection of mammalian cells with DNA," *Nucleic Acids Research* 15:1311–1326 (1987).

Curiel et al., "Gene Transfer to Respiratory Epithelial Cells via the Receptor–mediated Endocytosis Pathway," *Am. J. Respir. Cell. Mol. Biol.* 6:247–252 (1992).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Dolle et al., "5,7–Dimethoxy–3–(4–pyridinyl)quinoline is a Potent and Selective Inhibitor of Human Vascular –Type Platelet–Derived Growth Factor Receptor TyrosineKinase," *J. Med. Chem.* 37:2627–2629 (1994).

Dreborg et al., "Ch. 10—The chemistry and standardization of allergens," in *Handbook of Experimental Immunology—Volume 1: Immunochemistry*, 4th Ed., edited by Weir et al., Blackwell Scientific Publications, Oxford, England, pp. 10.1–10.28 (1986).

Engvall and Perlmann, "Enzyme–Linked Immunosorbent Assay, ELISA. III. Quantitation of Specific Antibodies by Enzyme–Labeled Anti–Immunoglobulin in Antigen–Coated Tubes," *J. Immunology* 109:129–135 (1972).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Fernandes et al., "Biochemical and Antitumor Effects of 5,8–Dideazaisopteroylglutamate, a Unique Quinazoline Inhibitor of Thymidylate Synthase," *Cancer Research* 43:117–1123 (1983).

Ferris et al., "Synthesis of Quinazoline Nucleosides from Ribose and Anthranilonitrile. Application of Phase–Transfer Catalysis in Nucleoside Synthesis," *J. Org. Chem.* 44(2):173–178 (1979).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Frohman et al., "Rapid production of full–length cDNAs from rare transcripts: Amplification using a single gene–specific oligonucleotide primer," *Proc. Nat'l Acad. Sci. USA* 85:8998–9002 (1988).

Fry et al., "A Specific Inhibitor of the Epidermal Growth Factor Receptor Tyrosine Kinase," *Science* 265:1093–1095 (1994).

Gavel and von Heijne, "Cleavage–site motifs in mitochondrial targeting peptides," *Prot. Engin.* 4:33–37 (1990).

Gentry and Lawton, "Characterization of Site–Specific Antibodies to the erbB Gene Product and EGF Receptor: Inhibition of Tyrosine Kinase Activity," *Virology* 152:421–431 (1986).

Gilman et al., "Isolation of sigma –28–specific promoters from *Bacillus subtilis* DNA," *Gene* 32:11–20 (1984).

Glick and Whitney, "Factors affecting the expression of foreign proteins in *Escherichia coli*," *Journal of Industrial Microbiology* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet.* 18:415–441 (1984).

Gryczan, "Ch. 10—Molecular Cloning in *Bacillus subtilis*," —in *The Molecular Biology of the Bacilli*, edited by Dubnau, Academic Press, New York, pp. 307–329 (1982).

Hamer and Walling, "Regulation In Vivo of a Cloned Mammalian Gene: Cadmium Induces the Transcription of a Mouse Metallothionein Gene in SV40 vectors," *J. of Molecular and Applied Genetics* 1:273–288 (1982).

Hammer et al., "Spontaneous Inflammatory Disease in Transgenic Rats Expressing HLA–B27 and Human $_2$m: An Animal Model of HLA–B27–Associated Human Disorders," *Cell* 63:1099–1112 (1990).

Hanks and Hunter, "The eukaryotic protein kinase superfamily: kinase (catalytic) domain structure and classification," *FASEB J.* 9:576–596 (1995).

Haslam et al., "Plecstrin domain homology," *Nature* 363:309–310 (1993).

Houdebine and Chourrout, "Transgenesis in Fish," *Experientia* 47:891–897 (1991).

Hurby et al., in *Synthetic Peptides: A User's Guide*, edited by Grant, Washington University School of Medicine, W.H. Freeman and Company, New York, pp. 289–307 (1992).

Innis et al., *PCR Protocols: A Guide to Methods and Applications*, edited by Michael A. Innis et al., Academic Press, San Diego (1990) (Table of Contents Only).

Izaki, *Jpn. J. Bacteriol.* 33:729–742 (1978) Abstract.

Jackman, "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Jasny, "Insect Viruses Invade Biotechnology," *Science* 238:1653 (1987).

John and Twitty, "Plasmids as Epidemiologic Markers in Nosocomial Gram–Negative Bacilli: Experience at a University and Review of the Literature," *Reviews of Infectious Diseases* 8:693–704 (1986).

Johnston and Hopper, "Isolation of the yeast regulatory gene GAL4 and analysis of its dosage effects on the galactose/melibiose regulon," *Proc. Natl. Acad. Sci. USA* 79:6971–6975 (1982).

Jones et al., "Quinazoline Antifolates Inhibiting Thymidylate Synthase: Varation of the Amino Acid," *J. Med. Chem.* 29:1114–1118 (1986).

Joyner et al., "Production of a mutation in mouse En–2 gene by homologous recombination in embryonic stem cells," *Nature* 338:153–156 (1989).

Kasprzak et al., "Location of a Contact Site Between Actin and Myosin in the Three–Dimensional Structure of the Acto–S1 Complex," *Biochemistry* 28:9230–9238 (1989).

Kendall and Cohen, "Plasmid Transfer in *Streptomyces lividans*: Identification of a kil–kor System Associated with the Transfer Region of PIJ101," *Journal of Bacteriology* 169:4177–4183 (1987).

Köhler and Milstein, "Continuous cultures of fused cells secreting antibody of predefined specificity," *Nature* 256:495–497 (1975).

Kohmura et al., "A Novel Nonreceptor Tyrosine Kinase, Srm: Cloning and Targeted Disruption," *Molecular and Cellular Biology.* 14(10):6915–6925 (1994).

Lee ad Skibo, "Active–Site–Directed Reductive Alkylation of Xanthine Oxidase by Imidazo[4,5–g]quinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Ley and Seng, "Synthesis Using Benzofuroxan," *Synthesis* 1975:415–422 (1975) Abstract.

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

MaGuire et al., "A New Series of PDGF Receptor Tyrosine Kinase Inhibitors: 3–Substituted Quinoline Derivatives," *J. Med. Chem.* 37:2129–2137 (1994).

Maniatis, "Ch. 11—Recombinant DNA Procedures in the Study of Eukaryotic Genes," in *Cell Biology: A Comprehensive Treatise, Volume 3, Gene Sequence Expression,* Academic Press, NY, pp. 563–608 (1980).

Maxwell et al., "$^{19}$F Nuclear Magnetic Resonance Imaging of Drug Distribution in Vivo: The Diposition of an Antifolate Anticancer Drug in Mice," *Magnetic Resonance in Medicine* 17:189–196 (1991).

Mayer and Baltimore, "Signalling through SH2 and SH3 domains," *Trends in Cell Biology* 3:8–13 (1993).

Mayer et al., "A novel viral oncogene with structural similarity to phospholipase C," *Nature* 332:272–275 (1988).

Meek et al., "The p53 tumour suppressor protein is phosphorylated at serine 389 by casein kinase II," *EMBO J.* 9:3253–3260 (1990).

McKnight, "Functional Relationships between Transcriptional Control Signals of the Thymidine Kinase Gene of Herpes Simplex Virus," *Cell* 31:355–365 (1982).

Miller et al., "An Insect Baculovirus Host–Vector System for High–Level Expression of Foreign Genes," in *Genetic Engineering: Principles and Methods,* edited by Setlow et al., Plenum Press, 8:277–298 (1986).

Miller, "Human gene therapy comes of age," *Nature* 357:455–460 (1992).

Mini et al., "Cytotoxic Effects of Folate Antagonists against Methotrexate–resistant Human Leukemic Lymphoblast CCRF–CEM Cell Lines," *Cancer Research* 45:325–330 (1985).

Mulligan, "The Basic Science of Gene Therapy," *Science* 260:926–932 (1993).

Nelson, "Detection of Acridinium Esters by Chemiluminescence," *Nonisotopic DNA Probe Techniques,* ed. Larry J. Kricka, (San Diego: Academic Press, Inc.) pp. 275–310 (1992).

Okayama and Berg, "A cDNA Cloning Vector That Permits Expression of cDNA Inserts in Mammalian Cells," *Molecular and Cellular Biology* 3:280–289 (1983).

Pawson and Schlessinger, "SH2 and SH3 domains," *Current Biology* 3(7):434–442 (1993).

Phillips and Castle, "Quino[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Ponting and Bork, "Pleckstrin's repeat performance: a novel domain in G–protein signaling?" *TIBS* 21:245–246 (1996).

Pursel et al., "Genetic Engineering of Livestock," *Science* 244:1281–1288 (1989).

Reece et al., "Pharmacokinetics of Trimetrexate Adminstered by Five–Day Continuous Infusion to Patients with Advanced Cancer," *Cancer Research* 47:2996–2999 (1987).

Robbins et al., "Two interdependent Basic Domains in Nucleoplasm Nuclear Targeting Sequence: Identification of a Class of Bipartite Nuclear Targeting Sequence," *Cell* 64:615–623 (1991).

Robertson, *Teratocarcinomas and embryonic stem cells: a practical approach,* IRL Press (1987) (Table of Contents).

Rubin, "*Drosophila melanogaster* as an Experimental Organism," *Science* 240:1453–1459 (1988).

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$, *Molecular and Cellular Biology* 6(12):4396–4408 (1986).

Sambrook et al., *Molecular Cloning: A Laboratory Manual,* $2^{nd}$ *Edition,* Cold Spring Harbor Laboratory Press (1989) (Table of Contents—All Three Volumes).

Sculier et al., "Role of an Intensive Care Unit (ICU) in a Medical Onocology Department," *Cancer Immunol. and Immunotherapy* 23:A65 at abstract No. 257 (1986).

Sikora et al., "Development of an Assay for the Estimation of $N^{10}$–Propargyl–5,8–dideazafolic Acid Polyglutamates in Tumor Cells," *Analytical Biochemistry* 172:344–355 (1988).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Silver et al., "Amino terminus of the yeast GAL4 gene product is sufficient for nuclear localization," *Proc. Natl. Acad. Sci. USA* 81:5951–5955 (1984).

Simons et al., "Gene Transfer into Sheep," *Bio/Technology* 6:179–182 (1988).

St. Groth and Scheidegger, "Production of Monoclonal Antibodies: Strategy and Tactics," *J. Immunol. Methods* 35:1–21 (1980).

Staley et al., "Inhibition of in vitro and in vivo (HT–29 colon adenocarcinoma cell growth by a c–src antisense expression vector," *Proc. Ann. Meet. Am. Assoc. Cancer Res.* 36:61 at abstract No. A362 (1995).

Sternberger et al., "The Unlabeled Antibody Enzyme Method of Immunohistochemistry: Preparation and Properties of Soluble Antigen–Antibody Complex (Horseradish Peroxidase–Antihorseradish Peroxidase) and its Use in Identification of Spirochetes," *J. Histochemistry and Cytochemistry* 18(5):315–333 (1970).

Superti–Furga et al., "Csk inhibition of c–Src activity requires both the SH2 and SH3 domains of Src," *EMBO J.* 12:2625–2634 (1993).

Superti–Furga et al., "A functional screen in yeast for regulators and antagonizers of heterologous protein tyrosine kinases," *Nature Biotech* 14:600–605 (1996).

Tijssen, *Practice and Theory of Enzyme Immunoassays: Laboratory Techniques in Biochemistry and Molecular Biology*, vol. 15, Elsevier Science Publishers, Amsterdam, The Netherlands (1985) (Table of Contents Only).

Tabor and Richardson, "DNA Sequence Analysis with a Modified Bacteriophase T7 DNA Polymerase," *Proc. Natl. Acad. Sci. USA* 84(14):4767–4771 (1987).

Towler et al., "The Biology of Enzymology of Eukaryotic Protein Acylation," *Annu. Rev. Biochem.* 57:69–99 (1988).

Ulmanen et al., "Transcription and Translation of Foreign Genes in *Bacillus subtilis* by the Aid of a Secretion Vector," *Journal of Bacteriology* 162:176–182 (1985).

Wilchek and Jakoby, "The Literature on Affinity Chromatography," *Methods in Enzymology* 34:3–10 (1974) (also referrred to as Jacoby).

Ward et al., "Construction and characterisation of a series of multi–copy promoter–probe plasmid vectors for Streptomyces using the aminoglycoside phosphotransferase gene from Tn5 as indicator," *Mol. Gen. Genet.* 203:468–478 (1986).

Yang et al., "In Vivo and In Vitro Gene Transfer to Mammaliam Somiatic Cells by Particle Bombardment," *Proc. Natl. Acad. Sci. USA* 87:9568–9572 (1990).

Stausberg, Robert, *National Cancer Institute, Cancer Genome Anatomy Project*, EMBL database entry HS1185621; accession number AA281242; Apr. 4, 1997.

Aoki et al., "The Novel Protein–tyrosine Phoshatase PTP20 is a Positive Regulator of PC12 Cell Neuronal Diffrentiation", *Journal of Biological Chemistry*, 271(46): 29422–29426 (Nov. 5, 1996), © The American Society for Biochemistry and Molecular Biology, Inc.

Saras et al., "Cloning and Characterization of PTPL1, a Protein Tyrosine Phosphatase with Similarities to Cytoskeletal–associated Proteins", *Journal of Biological Chemistry*, 269(39):24082–24089 (1994). © The American Society for Biochemistry and Molecular Biology, Inc.

Matthews et al., "Characterization of Hematopoietic Intracellular Protein Tyrosine Phosphatases: Description of a Phosphatase Containing an SH2 Domain and Another Enriched in Proline–, Glutamic Acid–, Serine–, and Threonine–Rich Sequences", *Molecular and Cellular Biology*, 12(5): 2396–2405 (May 1992) © American Society for Microbiology.

Maekawa et al., "Molecular cloning of a novel protein–tyrosine phosphatase containing a membrane–binding domain and GLGF repeats", *FEBS Letters*, 337: 200–206 (1994). © Federation of European Biochemical Societies.

Ley and Seng, "Synthesan unter Verwendung von Benzofuroxan" "Synthesis Using Benzofuroxen" *Synthesis* 1975:415–422 (1975).

Izaki, "Plasmid Induced Heavy Metal Resistance in Bacteria", *Japanese Journal of Bacteriology*, 33(6):729–742 (1978), © Japanese Society for Bacteriology.

* cited by examiner

DIAGNOSIS AND TREATMENT OF SAD RELATED DISORDERS

RELATED APPLICATIONS

This application claims priority to the U.S. Provisional Patent Application Ser. No. 60/049,914 by Plowman et al., entitled "Diagnosis and Treatment of SAD Related Disorders," and filed Jun. 18, 1997, which is incorporated herein by reference in its entirety, including any drawings.

FIELD OF THE INVENTION

The present invention relates to tyrosine kinases. In particular, the invention concerns a protein we have named SAD, nucleotide sequences encoding SAD, various products and assay methods that can be used for identifying compounds useful for the diagnosis and treatment of various SAD-related diseases and conditions, for example cell proliferative disorders.

BACKGROUND OF THE INVENTION

The following description is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function.

Protein kinases are one of the largest families of eukaryotic proteins with several hundred known members. These proteins share a 250–300 amino acid domain that can be subdivided into 12 distinct subdomains that comprise the common catalytic core structure. (Hanks and Hunter, *FASEB J.* 9:576–595, 1995). These conserved protein motifs have recently been exploited using PCR-based cloning strategies leading to a significant expansion of the known kinases. Multiple alignment of the sequences in the catalytic domain of protein kinases and subsequent phylogenetic analysis permits their segregation into a dendrogram. In this manner, related kinases are clustered into distinct branches or subfamilies including: tyrosine kinases, cyclic-nucleotide-dependent kinases, calcium/calmodulin kinases, cyclin-dependent kinases and MAP-kinases, serine-threonine kinases and several other less defined subfamilies.

Protein kinases can also be characterized by their location within the cell. Some kinases are transmembrane receptor-type proteins capable of directly altering their catalytic activity in response to the external environment such as the binding of a ligand. Others are non-receptor-type proteins lacking any transmembrane domain. They can be found in a variety of cellular compartments from the inner surface of the cell membrane to the nucleus.

Many kinases are involved in regulatory cascades wherein their substrates may include, but are not limited to, other kinases whose activities are regulated by their phosphorylation state. Ultimately the activity of some downstream effector is modulated by phosphorylation resulting from activation of such a pathway.

The known non-receptor tyrosine kinases (NR-TKs) can be classified in to several families: the Abl family (Abl, Arg), the Jak family (Jak1, Jak2, Jak3, Tyk2), the Fps family (Fes/Fps, Fer/Flk/Tyk3), the Syk family (Syk/PTK72, Zap70), the Tec Family (Tec, Tkx, Bmx/MKK2, Btk/Emb, Itk/Tsk/Emt), the Csk family (Csk, Ctk/MKK1), the Frk family (Frk/MKK3, Brk, Srm, Iyk), the Fak family (Fak, Pyk2), the Ack family (Ack, Ack2), and the Src family, which includes the members Src, Yes, Fyn, Lyn, Lck, Blk, Hck, Fgr and Yrk. (See Bolen, Oncogene 8:2025–2031, 1993.) Some NR-TKs are expressed ubiquitously, such as Src, Abl, and Jaks 1 and 2, while others are more restricted. For example, normal Fps, Syk and Zap70 expression is restricted to a subset of hematopeoetic cells. NR-TKs are known to be involved in a variety of normal cellular processes including cell proliferation and differentiation, cytokine signaling (the Jak family) and T-cell function (Zap70).

The expression of NR-TKs has also been associated with abnormal conditions such as cancer. The first tyrosine kinase to be discovered was the v-Src oncoprotein and many others (Yes, Fgr and Lck for example) have been identified as transforming proteins. Activation of Src and Yes are among the most consistent changes in human colon tumors (Staley, et al., Proc. Annu Meet Am Assoc Cancer Res 36:A362, 1995). A need exists to identify other NR-TKs whose activity results in such unwanted conditions as cancer as the identification and association of NR-TKs with a disorder is an important step in selection of pharmaceutical compounds for appropriate treatment.

SUMMARY OF THE INVENTION

Disclosed herein is a tyrosine kinase overexpressed in cancer cells which we have named SAD. The properties of SAD are described below. The present invention concerns SAD polypeptides, nucleic acids encoding such polypeptides, cells, tissues and animals containing such nucleic acids, antibodies to the polypeptides, assays utilizing the polypeptides, and methods relating to all of the foregoing.

A first aspect of the invention features an isolated, enriched, or purified nucleic acid molecule encoding a SAD polypeptide.

By "isolated" in reference to nucleic acid it is meant a polymer of 14, 17, 21 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90–95% pure at least) of nucleotide material naturally associated with it and thus is meant to be distinguished from isolated chromosomes.

By the use of the term "enriched" in reference to nucleic acid it is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated. The term is also chosen to distinguish clones already in existence which may encode SAD but which have not been isolated from other clones in a library of clones. Thus, the term covers clones encoding SAD which are isolated from other non-SAD clones.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA. The probe hybridizes (binds) to complementary sequences of cDNA.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

The term "hybridize" refers to a method of interacting a nucleic acid sequence with a DNA or RNA molecule in solution or on a solid support, such as cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Under highly stringent hybrydization conditions only highly complementary nucleic acid sequences hybridize. Preferably, such conditions prevent hybridization of nucleic acids having one or two mismatches out of 20 contiguous nucleotides.

Various low or high stringency hybridization conditions may be used depending upon the specificity and selectivity desired. Stringency is controlled by varying salt or denaturant concentrations. Examples of hybridization conditions are shown in the examples below. High stringent conditions may mean conditions that are at least as stringent as the following: hybridization in 50% formamide, 5×SSC, 50 mM $NaH_3PO_4$, pH 6.8, 0.5% SDS, 0.1 mg/mL sonicated salmon sperm DNA, and 5×Denhart solution at 42° C. overnight; washing with 2×SSC, 0.1% SDS at 45° C.; and washing with 0.2×SSC, 0.1% SDS at 45° C. Those skilled in the art will recognize how such conditions can be varied to vary specificity and selectivity.

A SAD polypeptide can be encoded by a full-length nucleic acid sequence or any portion of the full-length nucleic acid sequence. In preferred embodiments the isolated nucleic acid comprises, consists essentially of, or consists of a nucleic acid sequence set forth in SEQ ID NO:1, a nucleic acid sequence that hybridizes to the nucleic acid sequence set forth in SEQ ID NO:1 or a functional derivative (as defined below) of either. The nucleic acid may be isolated from a natural source by cDNA cloning or subtractive hybridization; the natural source may be mammalian (human) blood, semen, or tissue and the nucleic acid may be synthesized by the triester or other method or by using an automated DNA synthesizer.

The term "mammalian" refers to such organisms as mice, rats, rabbits, goats, more preferably monkeys and apes, and most preferably humans.

In other preferred embodiments, the nucleic acid molecule of the invention comprises a nucleotide sequence that (a) encodes a polypeptide having the full length amino acid sequence set forth in SEQ ID NO:2; (b) is the complement of the nucleotide sequence of (a);(c) hybridizes under highly stringent conditions to the nucleotide molecule of (a) and encodes a naturally occurring SAD polypeptide; (d) encodes an a SAD polypeptide having the full length amino acid sequence of the sequence set forth in SEQ ID NO:2, except that it lacks one or more of the following segments of amino acid residues: 1–55, 56–109, 120–212, 230–480, 481–488 of SEQ ID NO:2; (e) is the complement of the nucleotide sequence of (d); (f) encodes a polypeptide having the amino acid sequence set forth in SEQ ID NO:2 from amino acid residues 1–55, 56–109, 120–212, 230–480, 481–488 of SEQ ID NO:2; (g) is the complement of the nucleotide sequence of (f); (h) encodes a polypeptide having the full length amino acid sequence set forth in SEQ ID NO:2, except that it lacks one or more of the domains selected from the group consisting of an N-terminal domain, an SH2 domain, an SH3 domain, and a catalytic domain; or (i) is the complement of the nucleotide sequence of (h). The nucleic acid molecule of the invention is isolated, enriched, or purified from, preferably, a mammal, or most preferably from a human.

In yet other preferred embodiments the nucleic acid is an isolated conserved or unique region, for example those useful for the design of hybridization probes to facilitate identification and cloning of additional polypeptides, or for the design of PCR probes to facilitate cloning of additional polypeptides.

By "conserved nucleic acid regions", it is meant regions present on two or more nucleic acids encoding a SAD polypeptide, to which a particular nucleic acid sequence can hybridize under lower stringency conditions. Examples of lower stringency conditions suitable for screening for nucleic acids encoding SAD polypeptides are provided in Abe, et al. *J. Biol. Chem.* 19:13361 (1992) (hereby incorporated by reference herein in its entirety, including any drawings). Preferably, conserved regions differ by no more than 5 out of 20 contiguous nucleotides.

By "unique nucleic acid region" is meant a sequence present in a full length nucleic acid coding for a SAD polypeptide that is not present in a sequence coding for any other known naturally occurring polypeptide. Such regions preferably comprise 14, 17, 21 or more contiguous nucleotides present in the full length nucleic acid encoding a SAD polypeptide. In particular, a unique nucleic acid region is preferably of human origin.

In yet another aspect, the invention relates to a nucleic acid vector comprising a nucleic acid molecule encoding a SAD polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the SAD nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the SAD nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

The invention also features a nucleic acid probe for the detection of a nucleic acid encoding a SAD polypeptide in a sample. The term "nucleic acid probe" refers to a nucleic acid molecule that is complementary to and can bind a nucleic acid sequence encoding the amino acid sequence substantially similar to that set forth in SEQ ID NO:2.

The nucleic acid probe contains nucleic acid that will hybridize specifically to a sequence of at least 14, preferably 17, 20 or 22, contiguous nucleotides set forth in SEQ ID NO:1 or a functional derivative thereof. The probe is preferably at least 14, 17 or more bases in length and selected to hybridize specifically to a unique region of a SAD endocing nucleic acid.

In preferred embodiments the nucleic acid probe hybridizes to nucleic acid encoding at least 14 contiguous amino acids of the full-length sequence set forth in SEQ ID NO:1 or a functional derivative thereof. Various low or high stringency hybridization conditions may be used depending upon the specificity and selectivity desired. Under highly stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of SAD RNA in a sample by contacting the sample with a nucleic acid probe under conditions such that hybridization occurs and detecting the presence or amount of the probe bound to SAD RNA. The nucleic acid duplex formed between the probe and a nucleic acid sequence coding for a SAD polypeptide may be used in the identification of the sequence of the nucleic acid detected (for example see, Nelson et al., in Nonisotopic DNA Probe Techniques, p. 275 Academic Press, San Diego (Kricka, ed., 1992) hereby incorporated by reference herein in its entirety, including any drawings). Kits for performing such methods may be constructed to include a container having disposed therein a nucleic acid probe.

Another feature of the invention is a nucleic acid molecule as set forth in SEQ ID NO:1 or fragments thereof, comprising one or more regions that encode a SAD polypeptide or a SAD domain polypeptide, where the SAD polypeptide or the SAD domain polypeptide is fused to a non-SAD polypeptide. Such fused polypeptides include, for example, but are not limited to, a GST-fusion protein.

The invention also features recombinant nucleic acid, preferably in a cell or an organism. The recombinant nucleic acid may contain a sequence set forth in SEQ ID NO:1 or a functional derivative thereof and a vector or a promoter effective to initiate transcription in a host cell. The recombinant nucleic acid can alternatively contain a transcriptional initiation region functional in a cell, a sequence complimentary to an RNA sequence encoding a SAD polypeptide and a transcriptional termination region functional in a cell.

Another aspect of the invention relates to a recombinant cell or tissue comprising a nucleic acid molecule encoding a SAD polypeptide. The recombinant cell may comprise a nucleic acid molecule encoding either a SAD polypeptide; a SAD domain polypeptide; or a SAD polypeptide or SAD domain polypeptide fused to a non-SAD polypeptide.

The term "recombinant organism" refers to an organism that has a new combination of genes or nucleic acid molecules. A new combination of genes or nucleic acid molecules can be introduced to an organism using a wide array of nucleic acid manipulation techniques available to those skilled in the art.

The term "organism" relates to any living being comprised of a least one cell. An organism can be as simple as one eukaryotic cell or as complex as a mammal. Therefore, a recombinant organism can also be a recombinant cell, which may be a eukaryotic or a prokaryotic organism.

The term "eukaryote" refers to an organism comprised of cells that contain a nucleus. Eukaryotes are differentiated from "prokaryotes" which do not have a nucleus and lack other cellular structures found in eukaryotes, such as mitochondria and endoplasmic reticulum. Prokaryotes include unicellular organisms, such as bacteria, while eukaryotes are represented by yeast, invertebrates, and vertebrates.

The recombinant cell can harbor a nucleic acid vector that is extragenomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intragenomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Another aspect of the invention features an isolated, enriched, or purified SAD polypeptide.

By "SAD polypeptide" it is meant an amino acid sequence substantially similar to the sequence shown in SEQ ID NO:2, or fragments thereof. A sequence that is substantially similar will preferably have at least 90% identity (more preferably at least 95% and most preferably 99–1 100%) to the sequence of SEQ ID NO: 2.

The SAD polypeptides of the present invention preferably have a substantially similar biological activity to the protein encoded by the full length nucleic acid sequence set forth in SEQ ID NO:1 or to the proteins with amino acid sequence set forth in SEQ ID NO:2. By "biological activity" it is meant an activity of the SAD protein in a cell. The biological activity of the SAD is related to some of the activities of the cell which include, but are not limited to, cell proliferation motogenesis, metastasis, tumor escape, cell adhesion, transformation, or apoptosis.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

By "isolated" in reference to a polypeptide is meant a polymer of 6, 12, 18 or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of material naturally associated with it.

By the use of the term "enriched" in reference to a polypeptide it is meant that the specific amino acid sequence constitutes a significantly higher fraction (2–5 fold) of the total of amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased. The term significant here is used to indicate that the level of increase is useful to the person making such an increase, and generally means an increase relative to other amino acid sequences of about at least 2 fold, more preferably at least 5 to 10 fold or even more. The term also does not imply that there are no amino acid sequences from other sources. The other source amino acid sequences may, for example, comprise amino acid seqences encoded by a yeast or bacterial genome, or a cloning vector such as pUC19. The term is meant to cover only those situations in which a person has intervened to elevate the proportion of the desired amino acid sequences.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect the invention features an isolated, enriched, or purified SAD polypeptide fragment.

By "a SAD polypeptide fragment" it is meant an amino acid sequence that is less than the full-length SAD amino acid sequence shown in SEQ ID NO:2. Examples of fragments include SAD domains, SAD mutants and SAD-specific epitopes.

By "a SAD domain" it is meant a portion of the SAD polypeptide having homology to amino acid sequences from one or more known proteins wherein the sequence predicts some common function, interaction or activity. Well known examples of domains are the SH2 (Src Homology 2) domain (Sadowski, et al., *Mol. Cell. Biol.* 6:4396, 1986; Pawson and Schlessinger, *Curr. Biol.* 3:434, 1993), the SH3 domain (Mayer, et al., *Nature* 332:272, 1988; Pawson and Schlessinger, *Curr. Biol.* 3:434, 1993), and pleckstrin (PH) domain (Ponting, *TIBS* 21:245, 1996; Haslam, et al., *Nature* 363:309, 1993), all of which are domains that mediate protein:protein interaction, and the kinase catalytic domain (Hanks and Hunter, *FASEB J* 9:576–595, 1995). Computer programs designed to detect such homologies are well known in the art. The relative homology is at least 20%, more preferably at least 30% and most preferably at least 35%.

By a "SAD mutant" it is meant a SAD polypeptide which differs from the native sequence in that one or more amino acids have been changed, added or deleted. Changes in amino acids may be conservative or non-conservative. By "conservative" it is meant the substitution of an amino acid for one with similar properties such as charge, hydrophobicity, structure, etc. Examples of polypeptides encompassed by this term include, but are not limited to, (1) chimeric proteins which comprise a portion of the SAD polypeptide sequence fused to a non-SAD polypeptide sequence, for example a polypeptide sequence of glutathione-S-transferase (GST), (2) SAD proteins lacking a specific domain, for example the catalytic domain, and (3) SAD proteins having a point mutation. An SAD mutant will retain some useful function such as, for example, ligand binding, catalytic activity, or the ability to bind to a SAD specific antibody (as defined below).

By "SAD-specific epitope" it is meant a sequence of amino acids that is both antigenic and unique to SAD. SAD-specific epitope can be used to produce SAD-specific antibodies, as more fully described below. A particularly preferred epitope is amino acids 478 to 488 of SEQ ID NO:2.

By "recombinant SAD polypeptide" it is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

The polypeptide of the invention comprises an amino acid sequence having (a) the full length amino acid sequence set forth in SEQ ID NO:2; (b) the full length amino acid sequence of the sequence set forth in SEQ ID NO:2, except that it lacks one or more of the following segments of amino acid residues: 1–55, 56–109, 120–212, 230–480, 481–488 of SEQ ID NO:2; (c) the amino acid sequence set forth in SEQ ID NO:2 from amino acid residues, 1–55, 56–109, 120–212, 230–480, 481–488 of SEQ ID NO:2; or (d) the full length amino acid sequence set forth in SEQ ID NO:2 except that it lacks one or more of the domains selected from the group consisting of an N-terminal domain, an SH2 domain, an SH3 domain, and a catalytic domain.

In yet another aspect the invention features an antibody (e.g., a monoclonal or polyclonal antibody) having specific binding affinity to an SAD polypeptide or SAD polypeptide fragment. By "specific binding affinity" is meant that the antibody binds to target (SAD) polypeptides with greater affinity than it binds to other polypeptides under specified conditions. Antibodies having specific binding affinity to a SAD polypeptide may be used in methods for detecting the presence and/or amount of a SAD polypeptide in a sample by contacting the sample with the antibody under conditions such that an immunocomplex forms and detecting the presence and/or amount of the antibody conjugated to the SAD polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In another aspect the invention features a hybridoma which produces an antibody having specific binding affinity to a SAD polypeptide. By "hybridoma" is meant an immortalized cell line which is capable of secreting an antibody, for example a SAD antibody. In preferred embodiments the SAD antibody comprises a sequence of amino acids that is able to specifically bind a SAD polypeptide.

The invention features a method for identifying human cells containing a SAD polypeptide or a related sequence. The method involves identifying the novel polypeptide in human cells using techniques that are routine and standard in the art, such as those described herein for identifying SAD (e.g., cloning, Southern or Northern blot analysis, in situ hybridization, PCR amplification, etc.).

The invention also features methods of screening cells for natural binding partners of SAD polypeptides. By "natural binding partner" it is meant a protein that interacts with SAD. Binding partners include agonists, antagonists and downstream signaling molecules such as adaptor proteins and may be identified by techniques well known in the art such as co-immunoprecipitation or by using, for example, a two-hybrid screen. (Fields and Song, U.S. Pat. No. 5,283,173, issued Feb. 1, 1994 and, incorporated be reference herein.) The present invention also features the purified, isolated or enriched versions of the polypeptides identified by the methods described above.

In another aspect, the invention provides a method for identifying a substance capable of modulating SAD activity comprising the steps of (a) contacting a SAD polypeptide with a test substance; and (b) determining whether the substance alters the activity of said polypeptide.

The invention also features another method of identifying substances capable of modulating the function of a polypeptide. The method comprises the following steps: (a) expressing a SAD polypeptide in cells; (b) adding a compound to the cells; and (c) monitoring a change or an absence of a change in cell phenotype, cell proliferation, catalytic activity of the SAD polypeptide, and binding a natural binding partner.

The term "compound" includes small organic molecules including, but not limited to, oxindolinones, quinazolines, tyrphostins, quinoxalines, and those contained within extracts from natural sources. Examples of such compounds are included in section XII, below.

The term "function" refers to the cellular role of a serine-threonine protein kinase. The serine-threonine protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "modulates" refers to the ability of a compound to alter the function of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "catalytic activity," in the context of the invention, defines the ability of a protein kinase to phosphorylate a substrate. Catalytic activity can be measured, for example, by determining the amount of a substrate converted to a product as a function of time. Phosphorylation of a substrate occurs at the active-site of a protein kinase. The active-site is normally a cavity in which the substrate.

The term "substrate" as used herein refers to a molecule that is phoshorylated by or directly interacts with the protein kinase. The substrate is preferably a peptide and more preferably a protein. For example, in relation to the protein kinase RAF, preferred substrates are MEK and the MEK substrate MAPK.

The term "activates" refers to increasing the cellular function of a protein kinase. The protein kinase function is preferably the interaction with a natural binding partner or catalytic activity.

The term "inhibit" refers to decreasing the cellular function of a protein kinase. The protein kinase function is preferably the interaction with a natural binding partner or catalytic activity.

The term "modulates" also refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner.

The term "complex" refers to an assembly of at least two molecules bound to one another. Signal transduction complexes often contain at least two protein molecules bound to one another, either transiently or in succession. For instance, a receptor protein tyrosine kinase, GRB2, SOS, and RAF sequentially interact in response to a mitogenic ligand.

The term "expressing" as used herein refers to the production of a SAD polypeptide from a nucleic acid vector containing a SAD gene within a cell. The nucleic acid vector is transfected into cells using well known techniques in the art as described herein.

The term "adding" as used herein refers to administering a solution comprising a compound to the medium bathing cells. The solution comprising the compound can also comprise an agent, such as dimethyl sulfoxide, which facilitates the uptake of the compound into the cells.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "cell phenotype" refers to the outward appearance of a cell or tissue or the function of the cell or tissue. Examples of cell or tissue phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Change or the absence of change in cell phenotype is readily measured by techniques known in the art.

The term "cell proliferation" refers to the rate at which a group of cells divides. The number of cells growing in a vessel can be quantitated by a person skilled in the art when that person visually counts the number of cells in a defined area using a common light microscope. Alternatively, cell proliferation rates can be quantitated by laboratory apparatae that optically measure the density of cells in an appropriate medium.

The method can utilize any of the molecules disclosed in the invention. These molecules include nucleic acid molecules encoding SAD polypeptides, nucleic acid vectors, recombinant cells, polypeptides, or antibodies of the invention.

In a preferred embodiment, the invention provides a method for treating or preventing an abnormal condition by administering a compound which is a modular of SAD function in vitro. The abnormal condition preferably involves abnormality in SAD signal transduction pathway, and most preferably is cancer. Such compounds preferably show positive results in one or more in vitro assays for an activity corresponding to treatment of the disease or disorder in question (such as the assays described in Example 6 below). Examples of substances that can be screened for favorable activity are provided in section XII below.

The summary of the invention described above is non-limiting and other features and advantages of the invention will be apparent from the following detailed description, and from the claims.

DETAILED DESCRIPTION OF THE INVENTION

The present invention relates to the isolation and characterization of a new protein which we have called SAD, nucleotide sequences encoding SAD, various products and assay methods that can be used to identify compounds useful for the diagnosis and treatment of various SAD related diseases and conditions, for example cancer. Polypeptides derived from SAD and nucleic acids encoding such polypeptides may be produced using well known and standard synthesis techniques when given the sequences presented herein.

SAD is a tyrosine kinase with an apparent molecular weight of approximately 55 kDa. Primary sequence analysis shows that SAD is comprised of four domains: a domain at the N-terminus that shows no homology to any known sequence (the unique domain), an SH3 domain, an SH2 domain and a catalytic domain. The lack of a hydrophobic stretch of amino acids generally characterized as a trans-membrane region indicates that SAD is a non-receptor tyrosine kinase. A comparison of the amino acid sequences suggests that SAD is a member of the Frk family. Like some other members of this family, SAD lacks an N-terminal myristylation site and a C-terminal regulatory tyrosine characteristic of Src family members. It is most closely related to the murine NR-TK Srm (Kohmura, et al., *Mol. Cell. Bio.* 14(10):6915, 1994) with approximately 85% sequence homology in the catalytic domain. (Discussed in detail in the examples below.)

SAD was originally isolated from a human breast cancer cell line. Subsequent expression analysis of both normal tissues and cancer cell lines, shown in detail below, revealed that SAD has very limited expression in normal cells but is significantly overexpressed in a number of tumors. This suggests that SAD plays an important role in the growth and persistence of these cancers.

The polypeptide and nucleotide sequences of the invention can be used, therefore, to identify modulators of cell growth and survival which are useful in developing therapeutics for various cell proliferative disorders and conditions, and in particular cancers related to inappropriate SAD activity. Assays to identify compounds that act intracellularly to enhance or inhibit SAD activity can be developed by creating genetically engineered cell lines that express SAD nucleotide sequences, as is more fully discussed below.

I. Nucleic Acids Encoding SAD Polypeptides

A first aspect of the invention features nucleic acid sequences encoding a SAD polypeptide. Included within the scope of this invention are the functional equivalents of the herein-described isolated nucleic acid molecules. Functional equivalents or derivatives can be obtained in several ways. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the SAD gene could be synthesized to give a nucleic acid sequence significantly different from that shown in SEQ ID NO:1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the SAD nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the SAD genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

Functional equivalents or derivatives of SAD can also be obtained using nucleic acid molecules encoding one or more functional domains of the SAD polypeptide. For example, the SH2 domain of SAD functions as a phosphorylated tyrosine binding domain and a nucleic acid sequence encoding the SH2 domain alone or linked to other heterologous nucleic acid sequences can be considered a functional derivative of SAD. Other functional domains of SAD include, but are not limited to, the unique domain, the SH3 domain, and the catalytic domain. Nucleic acid sequences encoding these domains are shown in SEQ ID NO:1 as follows: N-terminal unique domain approximately 49–213; SH3 domain approximately 214–375; SH2 domain approximately 406–684; catalytic domain approximately 736–1488.

II. A Nucleic Acid Probe for the Detection of SAD

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (e.g., "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to "PCR Protocols, A Guide to Methods and Applications", edited by Innis et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (e.g., "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA as well as DNA probes and nucleic acids modified in the sugar, phosphate or even the base portion as long as the probe still retains the ability to specifically hybridize under conditions, as disclosed herein. Such probes are generated using techniques known in the art. The nucleic acid probe may be immobilized on a solid support. Examples of such solid supports include, but are not limited to, plastics such as polycarbonate, complex carbohydrates such as agarose and sepharose, acrylic resins, such as polyacrylamide and latex beads, and nitrocellulose. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method and Kit for Detecting SAD

One method of detecting the presence of SAD in a sample comprises (a) contacting the sample with one of the above-described nucleic acid probes, under conditions such that hybridization occurs, and (b) detecting the presence of the probe bound to a nucleic acid molecule in the sample. One skilled in the art would select the nucleic acid probe according to techniques known in the art as described above. Samples to be tested include but should not be limited to RNA samples of human tissue.

A kit for detecting the presence of SAD in a sample comprises at least one container having disposed therein tan above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatically labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising a SAD Nucleic Acid Molecule and Cells Containing These Constructs The present invention also relates to a recombinant DNA molecule comprising, 5' to 3', a promoter effective to initiate transcription in a host cell and one of the above-described nucleic acid molecules. In addition, the present invention relates to a recombinant DNA molecule comprising a vector and a nucleic acid molecule described herein. The present invention also relates to a nucleic acid molecule comprising a transcriptional region functional in a cell, a sequence complimentary to an RNA sequence encoding an amino acid sequence corresponding to a SAD polypeptide or functional derivative, and a transcriptional termination region functional in said cell. The above-described molecules may be isolated and/or purified DNA molecules.

The present invention also relates to a cell or organism that contains a SAD nucleic acid molecule as described herein and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but will in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a SAD gene may be obtained by the above-described cloning methods. This region may be retained for its transcriptional termination regulatory sequences, such as termination and polyadenylation.

Thus, by retaining the 3'-region naturally contiguous to the DNA sequence encoding a SAD gene, the transcriptional termination signals may be provided. Where the transcriptional termination signals are not satisfactorily functional in the expression host cell, then a 3' region functional in the host cell may be substituted.

Two DNA sequences (such as a promoter region sequence and a SAD sequence) are said to be operably linked if the nature of the linkage between the two DNA sequences does not (1) result in the introduction of a frame-shift mutation, (2) interfere with the ability of the promoter region sequence to direct the transcription of a SAD gene sequence, or (3) interfere with the ability of the a SAD gene sequence to be transcribed by the promoter region sequence. Thus, a promoter region would be operably linked to a DNA sequence if the promoter were capable of effecting transcription of that DNA sequence. Thus, transcriptional and translational signals recognized by an appropriate host are necessary to express a SAD gene.

The present invention encompasses the expression of a SAD gene (or a functional derivative thereof) in either prokaryotic or eukaryotic cells. Prokaryotic hosts are, generally, very efficient and convenient for the production of recombinant proteins and are, therefore, one type of preferred expression system for a SAD gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli* and those from genera such as Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express SAD (or a functional derivative thereof) in a prokaryotic cell, it is necessary to operably link a SAD sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage 1 ($P_L$, and $P_R$), the trp, recA, lacZ, lacI, and gal promoters of *E. coli*, the a-amylase (Ulmanen et al., *J. Bacteriol.* 162:176–182, 1985) and the sigma-28-specific promoters of *B. subtilis* (Gilman et al., *Gene Sequence* 32:11–20(1984)), the promoters of the bacteriophages of Bacillus (Gryczan, In: *The Molecular Biology of the Bacilli*, Academic Press, Inc., NY (1982)), and Streptomyces promoters (Ward et al., *Mol. Gen. Genet.* 203:468–478, 1986). Prokaryotic promoters are reviewed by Glick (*J. Ind. Microbiot.* 1:277–282, 1987); Cenatiempo (*Biochimie* 68:505–516, 1986); and Gottesman (*Ann. Rev. Genet.* 18:415–442, 1984).

Proper expression in a prokaryotic cell also requires the presence of a ribosome binding site upstream of the gene sequence-encoding sequence. Such ribosome binding sites are disclosed, for example, by Gold et at. (*Ann. Rev. Microbiol.* 35:365–404, 1981). The selection of control sequences, expression vectors, transformation methods, and the like, are dependent on the type of host cell used to express the gene.

As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the SAD peptide of interest. Suitable hosts may often include eukaryotic cells. Preferred eukaryotic hosts include, for example, yeast, fungi, insect cells, and mammalian cells either in vivo or in tissue culture. Mammalian cells which may be useful as hosts include HeLa cells, cells of fibroblast origin such as VERO, 3T3 or CHO-K1, or cells of lymphoid origin (such as 32D cells) and their derivatives. Preferred mammalian host cells include SP2/0 and J558L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459, 1988). Alternatively, baculovirus vectors can be engineered to express large amounts of SAD in insects cells (Jasny, *Science* 238:1653, 1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of SAD.

A particularly preferred yeast expression system is that utilizing Schizosaccharmocyces pombe. This system is useful for studying the activity of members of the Src family (Superti-Furga, et al., *EMBO J.* 12:2625, 1993) and other NR-TKs. Expression of SAD in this system is described in greater detail below.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of SAD in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288, 1982); the TK promoter of Herpes virus (McKnight, *Cell* 31:355–365, 1982); the SV40 early promoter (Benoist et al., *Nature* (London) 290:304–310, 1981); the yeast gal4 gene sequence promoter (Johnston et al., *Proc. Natl. Acad. Sci. USA* 79:6971–6975, 1982); Silver et al., *Proc. Natl. Acad. Sci. USA* 81:5951–5955, 1984).

Translation of eukaryotic mRNA is initiated at the codon which encodes the first methionine. For this reason, it is preferable to ensure that the linkage between a eukaryotic promoter and a DNA sequence which encodes SAD (or a functional derivative thereof) does not contain any intervening codons which are capable of encoding a methionine (i.e., AUG). The presence of such codons results either in a formation of a fusion protein (if the AUG codon is in the same reading frame as a SAD coding sequence) or a frame-shift mutation (if the AUG codon is not in the same reading frame as a SAD coding sequence).

A SAD nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Mol. Cell. Bio.* 3:280, 1983.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coil* (such as, for example, pBR322, ColEl, pSC101, pACYC 184, pVX. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable Streptomyces plasmids include p1J101 (Kendall et al., *J. Bacteriol.* 169:4177–4183,1987), and streptomyces bacteriophages such as fC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704, 1986), and Izaki (Jpn. *J. Bacteriol.* 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204, 1982); Bollon et at., *J. Clin. Hematol. Oncol.* 10:39–48, 1980); Maniatis, In: *Cell Biology: A Comprehensive Treatise*, Vol. 3, Gene Sequence Expression, Academic Press, NY, pp. 563–608 (1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of SAD or fragments or functional derivatives thereof. This can take place in the transformed cells as such, or following the induction of these cells to differentiate (for example, by administration of bromodeoxyuracil to neuroblastoma cells or the like). A variety of incubation conditions can be used to foster expression of the polypeptides of the present invention. The most preferred conditions are those which mimic physiological conditions.

V. SAD Polypeptides

Also a feature of the invention are SAD polypeptides. A variety of methodologies known in the art can be utilized to obtain the polypeptides of the present invention. They may be purified from tissues or cells which naturally produce them. Alternatively, the above-described isolated nucleic acid sequences can be used to express SAD protein recombinantly.

Any eukaryotic organism can be used as a source for the polypeptide of the invention, as long as the source organism naturally contains such a polypeptide. As used herein, "source organism" refers to the original organism from which the amino acid sequence is derived, regardless of the organism the protein is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

A SAD protein, like all proteins, is comprised of distinct functional units or domains. In eukaryotes, proteins sorted through the so-called vesicular pathway (bulk flow) usually have a signal sequence (also called a leader peptide) in the N-terminus, which is cleaved off after the translocation through the ER (endoplasmic reticulum) membrane. Some N-terminal signal sequences are not cleaved off, remaining as transmembrane segments, but it does not mean these proteins are retained in the ER; they can be further sorted and included in vesicles. SAD lacks a hydrophobic signal sequence and is classified as a non-receptor protein. Other motifs involved in targeting proteins to specific cellular locations include those selective for the mitochondrial matrix (Gavel and von Heijne, *Prot. Eng.* 4:33, 1990), the nucleus (Robbins, et al., *Cell* 64:615, 1991), peroxisomes, endoplasmic reticulum (Jackson, et al., *EMBO J* 9:3253, 1990), vesicular pathways (Bendiak, *Biophys. Res. Comm.* 170:879, 1990), glycosyl-phosphatidylinositol (GPI) lipid anchors, and lysosomal organelles, and motifs that target proteins to lipid membranes such as myristylation (Towler, et al., *Annu. Rev. Biochem.* 57:69, 1988) and farnesylation sites. The N-terminal 15 amino acids of the SAD protein conforms to the features which define a mitochondrial membrane protein with a bipartite structure of an N-terminal stretch of high arginine content involved in membrane targeting followed by the apolar sequence which signals translocation to the mitochondrial intermembrane space.

Non-receptor proteins generally function to transmit signals within the cell, either by providing sites for protein-:protein interactions or by having some catalytic activity (contained within a catalytic domain), often both. Methods of predicting the existence of these various domains are well known in the art. Protein:protein interaction domains can be identified by comparison to other proteins. The SH2 domain, for example is a protein domain of about 100 amino acids first identified as a conserved sequence region between the proteins Src and Fps (Sadowski, et al., *Mol. Cell. Bio.* 6:4396, 1986). Similar sequences were later found in many other intracellular signal-transducing proteins. SH2 domains function as regulatory modules of intracellular signaling cascades by interacting with high affinity to phosphotyrosine-containing proteins in a sequence specific and strictly phosphorylation-dependent manner (Mayer and Baltimore, *Trends Cell. Biol.* 3:8, 1993). Kinase catalytic domains can be identified by comparison to other known catalytic domains with kinase activity. See, for example Hanks and Hunter, *FASEB J.* 9:576–595, 1995.

Primary sequence analysis of the SAD amino acid sequence (shown in SEQ ID NO:2) reveals that it contains four distinct domains. These include an approximately 55 amino acid N-terminal unique domain (shown from amino acid number 1–55 of SEQ ID NO:2), an approximately 54 amino acid SH3 domain (shown from amino acid number 56–109 of SEQ ID NO:2), an approximately 93 amino acid SH2 domain (shown from amino acid number 120–212 of SEQ ID NO:2), an approximately 251 amino acid catalytic domain (amino acid number 230–480 of SEQ ID No:2), and a C-terminal tail of 8 amino acids (shown from amino acid 481–488 of SEQ ID NO:2).

These SAD domains have a variety of uses. An example of such a use is to make a polypeptide consisting of the SAD SH2 domain and a heterologous protein such as glutathione S-transferase (GST). Such a polypeptide, when expressed in a cell, is able to form complexes with the natural binding partner(s) of SAD but unable to transmit any signal further downstream into the cell, i.e., it would be signaling incompetent and thus would be useful for studying the biological relevance of SAD activity. (See, as an example, Gishizky, et al., *PNAS* :10889, 1995).

VI. An Antibody Having Binding Affinity to a SAD Polypeptide and a Hybridoma Containing the Antibody The present invention also relates to an antibody having specific binding affinity to a SAD polypeptide. The polypeptide may have the amino acid sequence set forth in SEQ ID NO:2, or a be fragment thereof, or at least 6 contiguous amino acids thereof. Such an antibody may be identified by comparing its binding affinity to a SAD polypeptide with its binding affinity to another polypeptide. Those which bind selectively to SAD would be chosen for use in methods requiring a distinction between SAD and other polypeptides. Such methods could include, but should not be limited to, the analysis of altered SAD expression in tissue containing other polypeptides and assay systems using whole cells.

A SAD peptide of the present invention can be used to produce antibodies or hybridomas. One skilled in the art will recognize that if an antibody is desired, such a peptide would be generated as described herein and used as an immunogen. A preferred SAD peptide in this respect is the sequence from amino acids 478 to 488 of SEQ ID NO:2. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., *J. Immunol. Methods* 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz, et al., *Exp. Cell Res.* 175:109–124, 1988). Hybridomas secreting the desired antibodies are cloned and the class and subclass is determined using procedures known in the art (Campbell, "Monoclonal Antibody Technology: Laboratory Techniques in Biochemistry and Molecular Biology", supra, 1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger, et al., *J. Histochem. Cytochem.* 18:315, 1970; Bayer, et at., *Meth. Enzym.* 62:308, 1979; Engval, et al., *Immunot.* 109:129, 1972; Goding, *J. Immunol. Meth.* 13:215, 1976). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., *Meth. Enzym.* 34, Academic Press, N.Y., 1974). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, NY, pp. 289–307 (1992), and Kaspczak et al., *Biochemistry* 28:9230–8(1989).

VII. An Antibody Based Method and Kit for Detecting SAD

The present invention encompasses a method of detecting a SAD polypeptide in a sample comprising incubating a test sample with one or more of the antibodies of the present invention and determining whether the antibody binds to the test sample. The method can include the steps of, for example: (a) contacting the sample with an above-described antibody, under conditions such that immunocomplexes form, and (b) detecting the presence of said antibody bound to the polypeptide. Altered levels, either an increase or decrease, of SAD in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is compatible with the system utilized.

A kit contains all the necessary reagents to carry out the previously described methods of detection. The kit may comprise: (i) a first container containing an above-described antibody, and (ii) second container containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will recognize that the antibodies described in the present invention can readily be incorporated into one of the established kit formats which are well known in the art.

VIII. Isolation of Natural Binding Partners of SAD

The present invention also relates to methods of detecting natural binding partners capable of binding to a SAD polypeptide. A natural binding partner of SAD may be, for example, a phosphotyrosine containing protein capable of interacting with the SAD SH2 domain as part of a signaling cascade. The binding partner(s) may be present within a complex mixture, for example, serum, body fluids, or cell extracts.

In general, methods for identifying natural binding partners comprise incubating a substance with a first polypeptide, SAD for the invention described herein, and detecting the presence of a substance bound to it. Preferred methods include the two-hybrid system of Fields and Song (supra) and co-immunoprecipitation wherein first polypeptide is allowed to bind to a natural binding partner, then the polypeptide complex is immunoprecipitated using antibodies specific for the first polypeptide. The natural binding partner can then be isolated and identified by techniques well known in the art.

IX. Identification of and Uses for Substances Capable of Modulating SAD Activity The present invention also relates to a method of detecting a substance capable of modulating SAD activity. Such substances can either enhance activity (agonists) or inhibit activity (antagonists). Agonists and antagonists can be peptides, antibodies, products from natural sources such as fungal or plant extracts or small molecular weight organic compounds. In general, small molecular weight organic compounds are preferred. Examples of classes of compounds that can be tested for SAD modulating activity are, for example but not limited to, oxindolines (see for example co-pending U.S. application Ser. No. 60/031,587, filed Dec. 5, 1996; No. 60/031,588, filed Dec. 5, 1996), thiazoles (co-pending U.S. application Ser. No. 60/033,522, filed Dec. 19, 1996; No. 08/660,900, filed Jun. 7, 1996now U.S. Pat. No. 5,883,110 ), and quinazolines (co-pending U.S. application Ser. No. 08/807,339, filed Feb. 28, 1997 now U.S. Pat. No. 6,103,728).

In general the method comprises incubating cells that produce SAD in the presence of a test substance and detecting changes in the level of SAD activity or SAD binding partner activity. A change in activity may be manifested by increased or decreased phosphorylation of a SAD polypeptide, increased or decreased phosphorylation of a SAD substrate, or increased or decreased biological response in cells. A method for detecting modulation of SAD activity using the phosphorylation of an artificial substrate is shown in the examples below. Biological responses can include, for example, proliferation, differentiation, survival, or motility. The substance thus identified would produce a change in activity indicative of the agonist or antagonist nature of the substance. Once the substance is identified it can be isolated using techniques well known in the art, if not already available in a purified form.

The present invention also encompasses a method of agonizing (stimulating) or antagonizing SAD associated activity in a mammal comprising administering to said mammal an agonist or antagonist to SAD in an amount sufficient to effect said agonism or antagonism. Also encompassed in the present application is a method of treating diseases in a mammal with an agonist or antagonist of SAD-related activity comprising administering the agonist or antagonist to a mammal in an amount sufficient to agonize or antagonize SAD associated function(s). The particular compound can be administered to a patient either by itself or in a pharmaceutical composition where it is mixed with suitable carriers or excipient(s). In treating a patient a therapeutically effective dose of the compound is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals. Cell culture assays and animal studies can be used for determining the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays by determining an $IC_{50}$ (i.e., the concentration of the test compound which achieves a half-maximal disruption of the protein complex, or a half-maximal inhibition of the cellular level and/or activity of a cellular component, ex. SAD). A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated. Particlar formulations suitable for parenteral administration of hydrophobic compounds can be found in U.S. Pat. No. 5,610,173, issued Mar. 11, 1997 and U.S. Provisional Application Ser. No. 60/039,870, filed Mar. 05, 1997, both of which are incorporated by reference herein in their entirety.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Small organic molecules may be directly administered intracellularly due to their hydrophobicity.

Pharmaceutical compositions suitable for use in the present invention include compositions wherein the active ingredients are contained in an amount effective to achieve its intended purpose. Determination of an effective amount is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

X. Transgenic Animals

Also contemplated by the invention are transgenic animals useful for the study of SAD activity in complex in vivo systems. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human SAD polypeptide. Native expression in an animal may be reduced by providing an amount of anti-sense RNA or DNA effective to reduce expression of the target gene.

A variety of methods are available for the production of transgenic animals associated with this invention. DNA sequences encoding SAD can be injected into the pronucleus of a fertilized egg before fusion of the male and female pronuclei, or injected into the nucleus of an embryonic cell (e.g., the nucleus of a two-cell embryo) following the initiation of cell division (Brinster, et al., *Proc. Nat. Acad. Sci. USA* 82: 4438, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47: 897–905, 1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., *Cell* 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. (See, for example, Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. (See Capecchi, *Science* 244: 1288, 1989.) Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153, 1989, the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. (See Houdebine and Chourrout, supra; Pursel, et al., *Science* 244:1281, 1989; and Simms, et al., *Bio/Technology* 6:179, 1988.)

Thus, the invention provides transgenic, nonhuman mammals containing a transgene encoding a SAD polypeptide or a gene effecting the expression of a SAD polypeptide. Such transgenic nonhuman mammals are particularly useful as an in vivo test system for studying the effects of introducing a SAD polypeptide, regulating the expression of a SAD polypeptide (i.e., through the introduction of additional genes, antisense nucleic acids, or ribozymes).

XI. Gene Therapy

SAD or its genetic sequences, both mutated and non-mutated, will also be useful in gene therapy (reviewed in Miller, *Nature* 357:455–460, (1992). Miller states that advances have resulted in practical approaches to human gene therapy that have demonstrated positive initial results. The basic science of gene therapy is described in Mulligan, *Science* 260:926, (1993). As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In one preferred embodiment, an expression vector containing a SAD coding sequence or a SAD mutant coding sequence as described above is inserted into cells, the cells are grown in vitro and then infused in large numbers into patients. In another preferred embodiment, a DNA segment containing a promoter of choice (for example a strong promoter) is transferred into cells containing an endogenous SAD in such a manner that the promoter segment enhances expression of the endogenous SAD gene (for example, the promoter segment is transferred to the cell such that it becomes directly linked to the endogenous SAD gene).

The gene therapy may involve the use of an adenovirus containing SAD cDNA targeted to an appropriate cell type, systemic SAD increase by implantation of engineered cells, injection with SAD virus, or injection of naked SAD DNA into appropriate cells or tissues.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant SAD protein into the targeted cell population (e.g., tumor cells or neurons). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., Nature 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. (Capecchi M R, Cell 22:479–88, 1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, Mol. Cell Biol. 7:2745–52, 1987); electroporation, wherein cells are exposed to large voltage pulses to introduce holes into the membrane (Chu G., et al., Nucleic Acids Res., 15:1311–26, 1987); lipofection/liposome fusion, wherein DNA is packaged into lipophilic vesicles which fuse with a target cell (Felgner P L., et al., Proc. Natl. Acad. Sci. USA. 84:7413–7, 1987)); and particle bombardment using DNA bound to small projectiles (Yang NS. et al. Proc. Natl. Acad. Sci. 87:9568–72, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. (Curiel, et al., Am. J. Respir. Cell. Mol. Biol., 6:247, 1992).

As used herein "gene transfer" means the process of introducing a foreign nucleic acid molecule into a cell. Gene transfer is commonly performed to enable the expression of a particular product encoded by the gene. The product may include a protein, polypeptide, antisense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

In another preferred embodiment, a vector having nucleic acid sequences encoding a SAD is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

XII. Compounds that Modulate the Function of SAD Proteins

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al.). The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976, published Aug. 1, 1996 by Ballinari et al. describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. No. 08/702,232, filed Aug. 23, 1996, entitled "Indolinone Combinatorial Libraries and Related Products and Methods for the Treatment of Disease" by Tang et al pending. and Ser. No. 08/485,323, filed Jun. 7, 1995, now U.S. Pat. No. 5,880,141, entitled "Benzylidene-Z-Indoline Compounds for the Treatment of Disease" by Tang et al. and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. Applications Ser. No. 08/702,232, filed Aug. 23, 1996, entitled "Indolinone Combinatorial Libraries and Related Products and Methods for the Treatment of Disease" by Tang et al., pending, Ser. No. 08/485,323, filed Jun. 7, 1995, entitled "Benzylidene-Z-Indoline Compounds for the Treatment of Disease" by Tang et al., now U.S. Pat. No. 5,880,141, and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating SAD activity include, but are not limited to, tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5, 316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325– 330 (1985); Phillips and Castle, *J. Het-erocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

EXAMPLES

The examples below are non-limiting and are merely representative of various aspects and features of the present invention. The examples below show the isolation and characterization of the novel protein SAD (Example 1), SAD expression in normal and tumor cells (Example 2), generation of SAD specific antibodies (Example 3), and recombinant expression in mammalian and yeast systems (Example 4). Also shown are assays useful for identifying compounds that modulate SAD activity (Example 5).

Example 1
Isolation and Characterization of SAD

This example describes the isolation and characterization of the non-receptor tyrosine kinase SAD. Initially we set out to identify novel members of the Src family, a group of nine related cytoplasmic tyrosine kinases which play key roles in several signal transduction pathways. Based on comparison of all known tyrosine kinases, we designed a pair of degenerate oligonucleotide primers that specifically recognize Src family members plus three more distantly related proteins Srm, Brk, and MKK3 or Frk (the Srm/Brk/Frk group). The sequence FGE/DVW (SEQ ID NO:3) is located near the amino terminus of the kinase domain and is unique to Src family members and the Srm/Brk/Frk group. The sequence WTAPE (SEQ ID NO:4) is located just amino terminal to the highly conserved DVWS motif of tyrosine kinases and is contained in the Src family and the Srm/Brk/Frk group as well as the Eph, Csk, Abl, and Fes families.

When we used the FGE/DVW and WTAPE primers in PCR amplification reactions with HME (human mammary epithelial) cell sscDNA as a template, we isolated multiple copies of known Src relatives as well as a novel DNA fragment (HME 1264) of 483 bp with homology to other kinases. The novel sequence was most similar to mouse Srm (GeneBank Accession #D26186) and the clone was designated human SAD.

A SAD probe was used to screen a cDNA library constructed from human breast cancer cell line mRNA to isolate two overlapping, independent clones spanning the kinase domain, but containing apparent introns and presumably arising from incompletely processed transcripts. The 5' end of the coding region was subsequently isolated by sequential RACE reactions from MCF7 RNA, and the entire coding region was re-isolated by PCR from HME cDNA.

Materials and Methods

Total RNA was isolated using the Guanidine Salts/Phenol extraction protocol of Chomczynski and Sacchi (P. Chomczynski and N. Sacchi, *Anal. Biochem.* 162, 156 (1987) from HME (human mammary epithelial) cells. This RNA was used as a template to generate single-stranded cDNAs using the Superscript Pre-amplification System for First Strand Synthesis kit purchased from GibcoBRL (Life Technologies, U.S.A.; Gerard, G F et al., *FOCUS* 11:66, 1989) under conditions recommended by manufacturer. A typical reaction used 10 $\mu$g total RNA or 2 $\mu$g poly(A)$^+$ RNA with 1.5 $\mu$g oligo(dT)$_{12-18}$ in a reaction volume of 60 $\mu$L. The product was treated with RNaseH and diluted to 100 $\mu$L with H$_2$0. For subsequent PCR amplification, 1–4 $\mu$L of these sscDNAs were used in each reaction.

Oligonucleotides were synthesized on an Applied Biosystems 394 DNA synthesizer using established phosphoramidite chemistry and were used unpurified after precipitation with ethanol. The degenerate oligonucleotide primers are:
FGE/DVW=5'-GGNCARTTYGGNGANGTNTGG-3' (SEQ ID NO:5) (sense) and
WTAPE=5'-CAGNGCNGCYTCNGGNGCNGTCCA-3' (SEQ ID NO:6) (antisense).
These primers were derived from the peptide sequences GQFG(E/D)VW (SEQ ID NO:7) (sense strand) and WTA-PEALL (SEQ ID NO:8) (antisense strand), respectively. Degenerate nucleotide residue designations are: N=A, C, G, or T; R=A or G; and Y=C or T. Using Src as a template, these primers produce a product of 480 bp.

A PCR reaction was performed using primers FGE/DVW and WTAPE applied to HME cell cDNA. The primers were added at a final concentration of 0.5 μM each to a mixture containing 10 mM Tris.HCl (pH8.3), 50 mM KCl, 1.5 mM MgCl$_2$, 200 μM each deoxynucleoside triphosphate, 0.001% gelatin, and 1.5 U AmpliTaq DNA Polymerase (Perkin-Elmer/Cetus), and 1–4 μL cDNA. Following 3 min denaturation at 94° C., the cycling conditions were 94° C. for 30 sec, 37° C. for 1 min, a 2 min ramp to 72° C., and 72° C. for 1 min for the first 3 cycles, followed by 94° C. for 30 sec, 60° C. for 1 min, and 72° C. for 1 min for 35 cycles. PCR fragments migrating at between 450–550 bp were isolated from 2% agarose gels, phosphorylated and repaired by treatment with T4 polynucleotide kinase and Klenow fragment, and blunt-end cloned into the EcoRV site of the vector pBluescriptSK+ (Stratagene U.S.A.).

Plasmid DNAs were isolated from single colonies by DNA minipreparations using QIAGEN columns and were sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., *J. Mol. Biol.* 215:403–10, 1990). A novel clone (HME1264) was isolated by PCR with primers FGE/DVW and WTAPE on single-stranded cDNA from HME cells as a template. This clone was subsequently designated as a fragment of human SAD.

A lambda ZapII (Stratagene Cloning Systems, La Jolla, Calif.) cDNA library was constructed using mRNA from a pool of breast carcinoma cell lines as a template for first strand cDNA synthesis with both oligo-(dT) and random priming (library created by Clonetech custom library synthesis department, Palo Alto, Calif.). The cell lines used for the pool were MCF7, HBL100, MDA-MB231, MDA-MB175IIV, MDA-MB435, MDA-MB453, MDA-MB468, BT20, T47D and SKBR3, all of which are available from the ATCC. Phage were screened on nitrocellulose filters with the random primed $^{32}$P-labeled insert from HME1264 at 2×10$^6$ cpm/mL in hybridization buffer containing 6×SSPE, 50% formamide, 2×Denhardt's reagent, 0.1% SDS, with 0.05 mg/mL denatured, fragmented salmon sperm DNA. After overnight hybridization at 42° C., filters were washed in 1×SSC, 0.1% SDS at 65° C. Two overlapping partial clones were isolated and sequenced through the coding region using manual sequencing with T7 polymerase and oligonucleotide primers (Tabor and Richardson, *Proc. Natl. Acad. Sci. U.S.A.* 84: 4767–71, 1987). These isolates encompass the kinase domain of SAD and extend from within an apparent intron 5' to the kinase domain and extend 3' to an in-frame termination codon, but are interrupted by four more apparent introns.

Two sequential 5' RACE (rapid amplification of cDNA ends) reactions (Frohman et al., *Proc. Natl. Acad. Sci. U.S.A.* 85: 8998, 1988) were subsequently used to isolate the 5' end of the coding region. Single strand cDNA was prepared as described above using the Superscript Pre-amplification System (GibcoBRL) using 6 μg total RNA from MCF7 cells as a template and gene specific primers 5556 (5'-AGTGAGCTTCATGTTGGCT-3' (SEQ ID NO:9)) for RACE 1 or 5848 (5'-GGTAGAGGCTGCCATCAG-3' (SEQ ID NO:10)) for RACE 2 to prime reverse transcription. Following treatment with RNase H, sscDNA was recovered using two sequential ethanol precipitations with ammonium acetate and carrier glycogen homopolymer tail of dA was added by treatment with deoxy-terminal transferase (GibcoBRL) and two reaction mixtures diluted to 50 μL with TE. Second strand cDNA synthesis by AmpliTaq DNA Polymerase (Perkin-Elmer/Cetus) was primed with 0.2 μM PENN(dT)$_{17}$ (5'-GACGATCGGAATTCGCGA(dT)$_{17}$-3' (SEQ ID NO:11)) using 1–5 μL of tailed cDNA as a template and buffer conditions given above. Following 5 min denaturation at 94° C., 1 min annealing at 50° C., and 40 min extension at 72° C., primers PENN (5'-GACGATCGGAATTCGCGA-3' (SEQ ID NO:12)) and 5555 (5'-CCCAGCCACAGGCCTTC-3' (SEQ ID NO:13)) were added at 1 μM and PCR done with cycling conditions of 94° C. for 30 s, 49° C. for 1 min, and 72° C. for 1 min, 45 sec for 40 cycles. A second, nested PCR was done using 0.2 μL of the initial PCR reaction as a template and primers PENN (see SEQ ID NO:12) and 5554 (5'-CCACACCTCCCCAAAGTA-3' (SEQ ID NO:14)) at 1 μM with an initial 3 min denaturation at 94° C., followed by cycling conditions of 94° C. for 30 s, 49° C. for 1 min, and 72° C. for 1 min, 45 sec for 35 cycles. PCR products were separated on 1% agarose gels and visualized by ethidium bromide staining and Southern hybridization using oligonucleotide 5557 (5'-TGGGAGCGGCCACACTCCGAATTCGCCCTT-3' (SEQ ID NO:15)) end-labeled with $^{32}$P. Reaction products of 500–700 bp were digested with EcoRI and cloned into the EcoRI site of pBluescriptSK+ (Stratagene U.S.A.), and positive clones were identified by colony hybridization with oligonucleotide 5557 as a probe. Clone 16A1 (which encompasses nucleotides 195 to 783 of SEQ ID NO:1) was isolated and sequenced by a combination of ABI and manual sequencing.

A second set of 5' RACE reactions was done based on the sequence of clone 16A1 using the procedure given above except as noted. Gene specific primers were 5848 (SEQ ID NO:10) for the first strand synthesis, 6118 (5'-GCCTGCGTGCGAAGATG-3' (SEQ ID NO:16)) for the first PCR, and 6119 (5'-CTTCGAGGGCACAGAGCC-3' (SEQ ID NO:17)) for the second PCR, and the probe for Southern and colony hybridization was random primed 32P-labeled insert from 16A1. PCR fragments migrating at between 250–450 bp were isolated from 2% agarose gels, phosphorylated and repaired by treatment with T4 polynucleotide kinase and Klenow fragment, and blunt-end cloned into the EcoRV site of the vector pBluescriptSK+ (Stratagene U.S.A.). Clone 20E2 (which encompasses nucleotides 1 to 267 of SEQ ID NO:1) was isolated and sequenced by a combination of ABI and manual sequencing.

The coding region of SAD was subsequently isolated from HME cDNA as two overlapping PCR fragments. Single stranded cDNA was prepared from poly(A)+RNA from HME cells using the Superscript Preamplification System (GibcoBRL) as described above. PCR with Ampli-Taq DNA Polymerase (Perkin-Elmer/Cetus) used 1–2 μL of cDNA as a template, an initial 3 min denaturation at 94° C., followed by cycling conditions of 94° C. for 30 s, 55° C. for 1 min, and 72° C. for 1 min, 45 sec for 30 cycles and the buffer conditions given above. Primers 6642 (5'-

ATGGAGCCGTTCCTCAGGAGG-3' (SEQ ID NO:18)) and 6644 (5'-TCACCCAGCTTCCTCCCAAGG-3' (SEQ ID NO:19)) were used to amplify an approximately 710 bp 5' fragment of SAD, and primers 6643 (5'-AGGCCAACTGGAAGCTGATCC-3' (SEQ ID NO:20) and 6645 (5'-GCTGGAGCCCAGAGCGTTGG-3' (SEQ ID NO:21)) were used to amplify an approximately 860 bp 3' fragment of SAD. PCR fragments were isolated from 1% agarose gels, phosphorylated and repaired by treatment with T4 polynucleotide kinase and Klenow fragment, and blunt-end cloned into the EcoRV site of the vector pBluescriptSK+ (Stratagene U.S.A.). Positive clones were identified by colony hybridization with the random primed 32P-labeled insert from 16A1 (for the 5'fragment) and the random primed 32P-labeled insert from HME1264 or 32P-labeled oligonucleotide 5557 (for the 3' fragment) as probes. The overlapping 5' and 3' PCR fragments were ligated together via the unique EcoRI site to give the full length SAD coding region. The complete sequence of the coding region of huma SAD was determined from overlapping 5' and 3' PCR clones amplified from cDNA prepared from HME cells. 5' noncoding sequence was determined from the overlapping RACE fragment 16A1. Sequence was determined manually on both strands using cycle sequencey dye-terminator kit with AmpliTaq DNA Polymerase, FS (ABI, Foster City, Calif.).

Results

The 1,548 bp human SAD (SAD_h) nucleotide sequence shown in SEQ ID NO:1 contains a single open reading frame encoding a polypeptide: of 488 amino acids. The SAD_h coding region is preceded by a 48 nucleotide 5'-untranslated region including an in-frame termination codon four codons before the initiating methionine and a 33 nucleotide 3'-untranslated region that includes two in-frame stop codons.

The sequences of SAD cDNAs were determined from overlapping PCR-amplified fragments from normal HME cell cDNA (nucleotides 49–1548), clones from a breast carcinoma cell lambda cDNA library (nucleotides 694–1548), and overlapping 5' RACE products from MCF7 cDNA (nucleotides 1–783) with the following sequence differences including some likely polymorphic sites. Ambiguities include a change of nucleotide 636 (see SEQ ID NO:1) from a C in the HME PCR clone to a T in the MCF& RACE product, nucleotide 1477 from a T in the HME PCR clone to a C in the breast carcinoma library, a deletion of nucleotides GT at positions 919–920 in the breast carcinoma library and apparent introns inserted at positions (relataive to SEQ ID NO:1) 694, 995, 1117, and 1334 in the breast carcinoma library.

The domain structure of SAD consists of an N-terminal unique domain followed by an SH3 domain, an SH2 domain and a kinase domain. This overall topology is shared by members of the Src, Srm/Brk/Mkk3, and Csk families. SAD is most similar to mouse Srm (GeneBank Accession #D26186) (Kohmura et al., Mol. Cell. Biol. 14: 6915–6925, 1994), a distant SRC relative of unknown function. SAD and Srm share sequence identities in the individual domains of 55% (unique region), 72% (SH3 domain), 78% (SH2 domain), and 85% (kinase domain). Unlike true Src family members, SAD and Srm lack both an N-terminal membrane attachment sequence and a potential C-terminal negative regulatory tyrosine. In addition, the characteristic HRDLRXAN (SEQ ID NO:22) sequence in the Src family kinase domain is HRDLAXRN (SEQ ID NO:23) in SAD and other Srm/Brk/Mkk3 group members. Like most other tyrosine kinases, SAD and Srm both contain a potential autophosphorylation site (380Y of SAD). The N-terminal sequences of SAD and Srm are similar with twenty identical residues out of the first twenty-two amino acids, but the extreme C-termini are quite distinct.

Available evidence suggests that SAD_h and Srm_m are distinct genes rather than species orthologues. Overall, the levels of homology between SAD_h and Srm_m listed above are comparable to those of close Src family members (for example Src_h and Yes_h), but lower than those of species counterparts (for example Src_h and Src_m). SAD_h and Srm_m also exhibit distinct expression patterns with SAD_h expression detected by PCR in the duodenum and perhaps testes, but not in other tissues tested, while the Srm_m expression was detected by Northern with highest levels in lung, liver, spleen, kidney, and testes (Kohmura et: al., Mol. Cell. Biol. 14: 6915–6925, 1994) (See Example 2 below.). Lastly, disruption of the Srm gene in mice has no detectable phenotype (Kohmura et al., Mol. Cell. Biol. 14: 6915), suggesting that other related proteins might compensate for its function.

Example 2

SAD Expression Analysis

Materials and Methods

RNA was isolated from a variety of human cell lines and fresh frozen normal tissues. (Tumor cell lines were obtained from Nick Scuidero, National Cancer Institute, Developmental Therapeutics Program, Rockville, Md.) Single stranded cDNA was synthesized from 10 $\mu$g of each RNA as described above using the Superscript Preamplification System (GibcoBRL). These single strand templates were then used in a 35 cycle PCR reaction using an annealing temperature of 65° C. with two SAD-specific oligonucleotides (5284: 5'-TCGCCAAGGAGATCCAGACAC-3' (SEQ ID NO:24), and 5285: 5'-GAAGTCAGCCACCTTGCAGGC-3' (SEQ ID NO:25)). Reaction products were electrophoresed on 2% agarose gels, stained with ethidium bromide and photographed on a UV light box. The relative intensity of the approximately 320-bp SAD-specific band was estimated for each sample. The results are shown with a numerical rating with 4 being the highest relative expression and 0 being the lowest.

Results

The SAD expression profile in normal human tissue and multiple cell lines of diverse neoplastic origin was determined by the semi-quantitative PCR assay using primers from sequences in the kinase domain. The results are included in Tables 1 and 2. In normal tissue samples (Table 1), modest SAD expression was detected in the duodenum and possible low levels in testes with all other samples negative. Much higher expression was found in a subset of cancer cell lines (Table 2) with the highest levels in some human colon tumor cell lines (HCT-15, SW480, and HT-29), an ovarian carcinoma (IGROV1), and an intestinal carcinoma (SNU-C2B) . Lesser expression of SAD was also seen in some other tumor cell lines derived from colon, breast, lung, ovary, and kidney as shown in Table 2.

TABLE 1

| Cell type | Origin | exp. level |
|---|---|---|
| duodenum | Normal Tissue | 2 |
| testes | Normal Tissue | 1? |

TABLE 1-continued

| Cell type | Origin | exp. level |
|---|---|---|
| brain | Normal Tissue | 0 |
| heart | Normal Tissue | 0 |
| kidney | Normal Tissue | 0 |
| lung | Normal Tissue | 0 |
| pancreas | Normal Tissue | 0 |
| placenta | Normal Tissue | 0 |
| salivary gland | Normal Tissue | 0 |
| skeletal muscle | Normal Tissue | 0 |
| spleen | Normal Tissue | 0 |
| stomach | Normal Tissue | 0 |
| thymus | Normal Tissue | 0 |
| cerebellum | Normal Tissue | 0 |
| liver | Normal Tissue | 0 |
| uterus | Normal Tissue | 0 |
| prostate | Normal Tissue | 0 |

Example 3
Generation of SAD-specific Immunoreagents

A SAD-specific antisera was raised in rabbits against a KLH-conjugated synthetic peptide derived from the C-terminal region of SAD (amino acids 478 to 488 of SEQ ID NO:2) with a C to S substitution at position 486 essentially as described in Gentry and Lawton, *Virology* 152:421, 1984.

Example 4
Recombinant Expression of SAD
Construction of Vectors

Expression constructs were generated by PCR-based mutagenesis in which a BamHI site was introduced upstream of the initiating Met giving a 5' untranslated sequence of 5'-GGATCCCCGGACC-3' (SEQ ID NO:26). An N-terminal hexahistidine tagged construct was also created by PCR with the coding sequence for MRGSHHH-HHH (SEQ ID NO:27) (ATGAGAGGATCGCATCACCATCACCATCAC, SEQ ID NO:28) followed by the second nucleotide of the SAD

TABLE 2

| Cell Line | Origin | exp. | Cell Line | Origin | exp |
|---|---|---|---|---|---|
| HCT-15 | colon | 4 | LOX IMVI | melanoma | 1? |
| IGROV1 | ovary | 4 | KATO III | gastric carcinoma | 0 |
| SW480 | colon adenocarcinoma | 3 | R-48 | meta. gast. adenocarcinoma | 0 |
| SNU-C2B | cecum primary carcinoma | 3 | HFL1 | lung, diploid | 0 |
| HT-29 | colon | 3 | HOP62 | lung | 0 |
| Colo 205 | colon carcinoma | 2 | OVCAR-4 | ovary | 0 |
| SW948 | colon adenocarcinoma | 2 | SKOV3 | ovary | 0 |
| HCT116 | colon | 2 | NCIH23 | lung | 0 |
| EKVX | lung | 2 | NCI-H460 | lung | 0 |
| NCI-H23 | lung | 2 | COLO205 | colon | 0 |
| HCC-2998 | colon | 2 | NCI-H460 | lung | 0 |
| HCT 116 | colon | 2 | A549/ATCC | lung | 0 |
| MCF7 | breast | 2 | HOP-62 | lung | 0 |
| T-47D | breast | 2 | COLO 205 | colon | 0 |
| OVCAR-3 | ovary | 2 | KM-12 | colon | 0 |
| OVCAR-5 | ovary | 2 | MDA-MB-231 | breast | 0 |
| OVCAR-8 | ovary | 2 | MDA-MB-435 | breast | 0 |
| SN12C | renal | 2 | MDA-N | breast | 0 |
| ACHN | renal | 2 | BT-549 | breast | 0 |
| 786-0 | renal | 2 | SNB-19 | CNS | 0 |
| TK-10 | renal | 2 | SNB-75 | CNS | 0 |
| HT29 | colon adenocarcinoma | 1 | U251 | CNS | 0 |
| RF-1 | gastric carcinoma | 1 | SF-268 | CNS | 0 |
| AGS | gastric carcinoma | 1 | SF-295 | CNS | 0 |
| EKVX | lung | 1 | CCRF-CEM | leukemia | 0 |
| HOP-92 | lung | 1 | MOLT-4 | leukemia | 0 |
| NCI-H226 | lung | 1 | HL-60 (TB) | leukemia | 0 |
| NCI-H322M | lung | 1 | RPMI 8226 | leukemia | 0 |
| MCF7/ADR | breast | 1 | SR | leukemia | 0 |
| OVCAR-4 | ovary | 1 | UO-31 | renal | 0 |
| SF-539 | CNS | 1 | A498 | renal | 0 |
| K-562 | leukemia | 1 | Caki-1 | renal | 0 |
| RXF 393 | renal | 1 | SK-MEL-2 | melanoma | 0 |
| Calu-3 | lung adenocarcinoma | 1? | SK-MEL-5 | melanoma | 0 |
| NCI-H522 | lung | 1? | SK-MEL-28 | melanoma | 0 |
| SW620 | colon | 1? | UACC-62 | melanoma | 0 |
| Hs 578T | breast | 1? | UACC-257 | melanoma | 0 |
| SK-OV-3 | ovary | 1? | M14 | melanoma | 0 | coding sequence (a glutamate). Proteins tagged with this sequence can be recognized by the RGS•His Antibody (QIAGEN Inc.) and affinity purified with Ni-NTA resin (QIAGEN Inc.). These constructs were cloned into the 5'-BamHI and 3'-EcoRI sites of pBluescriptSK+ (Stratagene U.S.A.) and the 5'-BamHI and 3'-XhoI sites of the mammalian expression pcDNA3 (Invitrogen) for transient expression analysis.

The SpeI-XhoI full length SAD constructs were also cloned from pBluescriptSK+ (Stratagene U.S.A.) into the yeast expression vector pRSP (Superti-Furga et al., *EMBO J.* 12:2625–2634). This vector contains a thiamine-repressible promoter in a shuttle vector for inducible expression in Schizosaccharomyces pombe. This system has been useful in studies of SRC family members for testing negative regulation by CSK, screening for additional regulators, and purifying recombinant: protein (Superti-Furga et al., *EMBO J.* 12:2625–2634; Superti-Furga et al., *Nature Biotech.* 14:600–605).

Transient Expression of Sad in Mammalian Cells

The pcDNA3 expression plasmids (5 μg DNA/60 mm plate) containing the unmodified and hexahistidine-tagged SAD genes were introduced into 293 cells with lipofectamine (Gibco BRL). After 48 hours, the cells were harvested in 0.25 mL RIPA (20 mM Tris-Cl pH 7.5, 150 mM NaCl, 1% Triton X-100, 1% deoxycholate, 0.1% SDS, 1 mM DTT, 1 mM sodium vanadate, 1 mM phenylmethylsulfonyl fluoride, 2 μg/mL aprotinin, 1 μ/mL leupeptin, and 25 μg/mL trypsin inhibitor). Sample aliquots were resolved by SDS polyacrylamide gel electrophoresis (PAGE) on 10% acrylamide gels and electrophoretically transferred to nitrocellulose. Non-specific binding was blocked by preincubating blots in Blotto (Tris buffered saline containing 5% w/v non-fat dried milk and 0.1% v/v Tween-20), and recombinant protein was detected using affinity-purified SAD-specific polyclonal antibody and peroxidase-linked secondary antibody with the ECL kit (Amersham Life Science). Hexahistidine tagged protein was also detected using RGS•His Antibody (QIAGEN Inc.). Phosphotyrosine-containing proteins were detected by Western blotting with monoclonal antibody 4G10 (Upstate Biotechnology) with 3% BSA as the blocking agent.

Affinity purified antipeptide antibody raised against the C-terminus of SAD (see Example 3) recognized a specific ~55 kDa protein in transfected 293 cells with greater than 90% of the expressed protein being RIPA-insoluble. This molecular weight is consistent with the molecular weight predicted based on SAD's primary amino acid sequence (54,510 kD). SAD-transfected cells contain a prominent approximately 55 kDa tyrosine phosphorylated protein that is absent in vector controls. The phosphorylated protein is most likely SAD itself because the band is clearly detected in IP-Westerns using anti-SAD crosslinked to protein A beads and 4G10 as the blotting antibody although anti-SAD only inefficiently immunoprecipitates.

Expression of Recombinant SAD in Schizosaccharomyces Pombe

S. pombe was used to express recombinant SAD as an approach to studying its function and regulation since this expression system has proven useful for studying Src family members (Superti-Furga et al., *EMBO J.* 12, 2625–2634; Superti-Furga et al., *Nature Biotech.* 14, 600–605). S. pombe strain SP200 (h-s leu1.32 ura4 ade210) was grown as described and transformations with pRSP expression plasmids were done by the lithium acetate method (Moreno et al., 1991; Superti-Furga et al., *EMBO J.* 12, 2625–2634). Cells were grown in the presence of 1 μM thiamine to repress expression from the nmt1 promoter or in the absence of thiamine to induce expression.

Under derepressing conditions, SAD-expressing strains show no growth defect compared to vector controls in either liquid culture or solid media. This result contrasts with the toxicity caused by expression of several other tyrosine kinases including Src and Frk. SAD protein can be detected in these strains as a weak band on Western blots using the polyclonal antibody against the C-terminus. On anti-phosphotyrosine Western blots, SAD itself is the only detectable phosphotyrosine-containing protein, however in the presence of pervanadate, cellular proteins are also phosphorylated. This observation contrasts with the results seen for Src and MKK3 which phosphorylate many yeast proteins even in the absence of phosphatase inhibitors. These findings suggest that SAD exhibits relatively limited substrate specificity and autophosphorylates itself. These results are consistent with the transient expression experiments in 293 cells.

Example 5

Assay for SAD Kinase Activity

The example below describes an in vitro assay for SAD kinase activity. The assay is useful for the identification of modulators of SAD activity.

Materials and Methods

S. pombe expressing hexahistidine-tagged SAD were harvested by centrifugation and lysed by the glass bead method (Superti-Furga et al., *EMBO J.* 12, 2625–2634) in NP-40 lysis buffer (50 mM Tris-Cl pH 7.5, 150 mM NaCl, 1% NP-40, 5 mM 2-mercaptoethanol, 1 mM sodium vanadate, 1 mM phenylmethylsulfonyl fluoride, 2 μg/mL aprotinin, 1 μg/mL leupeptin, and 25 μg/mL trypsin inhibitor). Immunoprecipitations were done by mixing yeast extract (100 μg total protein in 100 μL NP-40 lysis buffer) with 0.6 μg the RGS•His Antibody (QIAGEN Inc.) and 10 μL Protein A/G agarose (Upstate Biotechnology) for 3 hrs at 4° C. IP complexes were washed four times in 1 mL lysis buffer and once in 1 mL kinase buffer (20 mM Na-HEPES pH 7.5, 10 mM $MnCl_2$, 2 mM 2-mercaptoethanol, and 10 μM sodium vanadate). Kinase assays were for 10 min at 30° C. in 40 μL kinase buffer containing 15 μM ATP, 0.5 μCi g-32P-ATP, and either 3 μg denatured enolase or 10 μg poly-Glu-Tyr (4:1) as the substrate. Extracts were assayed using 2–10 μg total protein per reaction and IP complexes were assayed using 5 μL Protein A/G beads per assay. Reactions were terminated by the addition of SDS sample buffer and the samples were resolved on an 10% SDS polyacrylamide gel and visualized by autoradiography.

Results

SAD was able to phosphorylate both denatured enolase and poly-Glu-Tyr in vitro. Phosphorylation of both substrates was detected in crude yeast lysates expressing SAD but not in lysates from vector control strains. In addition, anti-His IP complexes from SAD-expressing strains but not control strains phosphorylated both denatured enolase and poly-Glu-Tyr.

Example 6

Screening Systems for the Identification of Inhibitors of SAD Activity

Assays may be performed in vitro or in vivo and are described in detail herein or can be obtained by modifying existing assays, such as the growth assay described in patent application Ser. No. 08/487,088 filed Jun. 7, 1995, by Tang et al., and entitled "Novel Pharmaceutical Compounds," abandoned or the assays described in patent application Ser. No. 60/005,167 filed Oct. 13, 1995 by Seedorf et al., and entitled "Diagnosis and Treatment of TKA-1 related disorders," all of which are hereby incorporated herein by reference in their entirety including any drawings. Another assay which could be modified to use the genes of the present invention is described in International Application No. WO 94/23039, published Oct. 13, 1994, hereby incorporated herein by reference in its entirety including any drawings. . Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase (Fields and Song, U.S. Pat. No. 5,283,173, issued Feb. 1, 1994, incorporated by reference herein, including any drawings).

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acide alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified to form a second nucleic acid sequence, encoding the same polypeptide as endoded by the first nucleic acid sequences, using routine procedures and without undue experimentation. Thus, all possible nucleic acids that encode the claimed peptides and proteins are also fully described herein, as if all were written out in full taking into account the codon usage, especially that preferred in humans. Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a β-turn, away from the active site of the polypeptide. Also changes such as deletions (e.g., removal of a segment of the polypeptide, or in the corresponding nucleic acid sequence encoding such polypeptide, which does not affect the active site) and additions (e.g., addition of more amino acids to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

Other embodiments are within the following claims.

What is claimed is:

1. An isolated or purified nucleic acid molecule comprising a nucleotide sequence that
   (a) encodes a polypeptide comprising the full length amino acid sequence set forth in SEQ ID NO:2; or
   (b) is the nucleic acid that is completely complementary to the nucleotide sequence of (a).

2. An isolated or purified nucleic acid molecule comprising a nucleotide sequence that
   (a) encodes a polypeptide comprising the amino acid sequence set forth in amino acid residues 230–480 of SEQ ID NO:2; or
   (b) is the nucleic acid that is completely complementary to the nucleotide sequence of (a).

3. The nucleic acid molecule of claim 1 or 2, wherein said nucleic acid molecule is isolated or purified from a mammal.

4. The nucleic acid molecule of claim 3, wherein said mammal is a human.

5. A nucleic acid probe comprising the isolated, or purified nucleic acid molecule of claim 1 or 2.

6. A nucleic acid molecule comprising a nucleotide sequence that encodes a chimeric protein comprising a non-SAD polypeptide fused to either a SAD polypeptide or a SAD catalytic domain, wherein the amino acid sequence of said SAD polypeptide is set forth in SEQ ID NO: 2 and wherein said SAD catalytic domain consists of amino acid residues 230–480 of SEQ ID NO: 2.

7. The nucleic acid molecule of claim 6, wherein said non-SAD polypeptide is glutathione-S-transferase (GST).

8. A recombinant cell comprising the nucleic acid molecule of claim 6.

9. A nucleic acid vector comprising
   (a) a nucleotide sequence encoding a polypeptide comprising the full length amino acid sequence set forth in SEQ ID NO: 2; and
   (b) a promoter effective to initiate transcription in a host cell.

10. A nucleic acid vector comprising
    (a) a nucleotide sequence encoding amino acid residues 230–480 of SEQ ID NO: 2; and
    (b) a promoter effective to initiate transcription in a cell.

11. The nucleic acid vector of claim 10, further comprising at least one of either a transcriptional initiation region or a transcriptional termination region.

12. A double-stranded nucleic acid vector comprising
    (a) a nucleotide sequence encoding amino acid residues 230–480 of SEQ ID NO: 2; and
    (b) a promoter effective to initiate transcription in a cell.

13. The double-stranded nucleic acid vector of claim 12, further comprising at least one of either a transcriptional initiation region or a transcriptional termination region.

14. An isolated or purified nucleic acid molecule comprising the nucleotide sequence set forth in SEQ ID NO: 1.

15. A recombinant cell comprising the nucleic acid molecule of claim 1 or 2.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
        (A) LENGTH:     1548 base pairs
        (B) TYPE:       nucleic acid
        (C) STRANDEDNESS: single
        (D) TOPOLOGY:   linear (xi) SEQUENCE DESCRIPTION: SEQ ID NO: 1:

```
GCTCGCGGGC TCCCATGGCC CTCGGGCCCA GCGTGGTGAC CCCGGGGGAT GGAGCCGTTC      60
CTCAGGAGGC GGCTGGCCTT CCTGTCCTTC TTCTGGGACA AGATCTGGCC GGCGGGCGGC     120
GAGCCGGACC ATGGCACCCC CGGGTCCCTG ACCCCAACA  CTGACCCAGT GCCCACGCTC     180
CCCGCCGAGC CTTGCAGCCC CTTCCCTCAG CTCTTCCTTG CGCTCTATGA CTTCACGGCG     240
CGGTGTGGCG GGGAGCTGAG TGTCCGCCGC GGGGACAGGC TCTGTGCCCT CGAAGAGGGG     300
GGCGGCTACA TCTTCGCACG CAGGCTTTCG GGCCAGCCCA GCGCCGGGCT CGTGCCCATC     360
ACCCACGTGG CCAAGGCTTC TCCTGAGACG CTCTCAGACC AACCCTGGTA CTTTAGCGGG     420
GTCAGTCGGA CCCAGGCACA GCAGCTGCTC CTCTCCCCAC CCAACGAACC AGGGGCCTTC     480
CTCATCCGGC CAGCGAGAG  CAGCCTCGGG GGCTACTCAC TGTCAGTCCG GGCCCAGGCC     540
AAGGTCTGCC ACTACCGGGT CTCCATGGCA GCTGATGGCA GCCTCTACCT GCAGAAGGGA     600
CGGCTCTTTC CCGGCCTGGA GGAGCTGCTC ACCTACTACA AGGCCAACTG GAAGCTGATC     660
CAGAACCCCC TGCTGCAGCC CTGCATGCCC CAGAAGGCCC CGAGGCAGGA CGTGTGGGAG     720
CGGCCACACT CCGAATTCGC CCTTGGGAGG AAGCTGGGTG AAGGCTACTT TGGGGAGGTG     780
TGGGAAGGCC TGTGGCTGGG CTCCCTGCCC GTGGCGATCA AGGTCATCAA GTCAGCCAAC     840
ATGAAGCTCA CTGACCTCGC CAAGGAGATC CAGACACTGA AGGGCCTGCG GCACGAGCGG     900
CTCATCCGGC TGCACGCAGT GTGCTCGGGC GGGGAGCCTG TGTACATAGT CACGGAACTC     960
ATGCGCAAGG GGAACCTGCA GGCCTTCCTG GGCACCCCG  AGGGCCGGGC CCTGCGTCTG    1020
CCGCCACTCC TGGGCTTTGC CTGCCAGGTG GCTGAGGGCA TGAGCTACCT GGAGGAGCAG    1080
CGCGTTGTGC ACCGGGACTT GGCCGCCCGG AACGTGCTCG TGGACGACGG CCTGGCCTGC    1140
AAGGTGGCTG ACTTCGGCCT GGCCCGGCTG CTCAAGGACG ACATCTACTC CCCGAGCAGC    1200
AGCTCCAAGA TCCCGGTCAA GTGGACAGCG CCTGAGGCGG CCAATTATCG TGTCTTCTCC    1260
CAGAAGTCAG ACGTCTGGTC CTTCGGCGTC CTGCTGCACG AGGTTTTCAC CTATGGCCAG    1320
TGTCCCTATG AAGGGATGAC CAACCACGAG ACGCTGCAGC AGATCATGCG AGGGTACCGG    1380
CTGCCGCGCC CGGCTGCCTG CCCGGCGGAG GTCTACGTGC TCATGCTGGA GTGCTGGAGG    1440
AGCAGCCCCG AGGAACGGCC CTCCTTTGCC ACGCTGCGGG AGAAGCTGCA CGCCATCCAC    1500
AGATGCCACC CCTGAGTCCT CACGTGACCC AACGCTCTGG GCTCCAGC                 1548
```

(2) INFORMATION FOR SEQ ID NO: 2:

(i) SEQUENCE CHARACTERISTICS:
        (A) LENGTH:      488 amino acids
        (B) TYPE:        amino acid
        (C) STRANDEDNESS: single
        (D) TOPOLOGY:    linear (ii) MOLECULE TYPE:    peptide (xi) SEQUENCE DESCRIPTION: SEQ ID NO: 2:

```
Met Glu Pro Phe Leu Arg Arg Arg Leu Ala Phe Leu Ser Phe Phe Trp
 1               5                  10                  15

Asp Lys Ile Trp Pro Ala Gly Gly Glu Pro Asp His Gly Thr Pro Gly
            20                  25                  30

Ser Leu Asp Pro Asn Thr Asp Pro Val Pro Thr Leu Pro Ala Glu Pro
        35                  40                  45

Cys Ser Pro Phe Pro Gln Leu Phe Leu Ala Leu Tyr Asp Phe Thr Ala
    50                  55                  60
```

-continued

```
Arg Cys Gly Gly Glu Leu Ser Val Arg Arg Gly Asp Arg Leu Cys Ala
 65                  70                  75                  80

Leu Glu Glu Gly Gly Gly Tyr Ile Phe Ala Arg Arg Leu Ser Gly Gln
                 85                  90                  95

Pro Ser Ala Gly Leu Val Pro Ile Thr His Val Ala Lys Ala Ser Pro
            100                 105                 110

Glu Thr Leu Ser Asp Gln Pro Trp Tyr Phe Ser Gly Val Ser Arg Thr
            115                 120                 125

Gln Ala Gln Gln Leu Leu Ser Pro Asn Glu Pro Gly Ala Phe
130                 135                 140

Leu Ile Arg Pro Ser Glu Ser Ser Leu Gly Gly Tyr Ser Leu Ser Val
145                 150                 155                 160

Arg Ala Gln Ala Lys Val Cys His Tyr Arg Val Ser Met Ala Ala Asp
                165                 170                 175

Gly Ser Leu Tyr Leu Gln Lys Gly Arg Leu Phe Pro Gly Leu Glu Glu
                180                 185                 190

Leu Leu Thr Tyr Tyr Lys Ala Asn Trp Lys Leu Ile Gln Asn Pro Leu
                195                 200                 205

Leu Gln Pro Cys Met Pro Gln Lys Ala Pro Arg Gln Asp Val Trp Glu
            210                 215                 220

Arg Pro His Ser Glu Phe Ala Leu Gly Arg Lys Leu Gly Glu Gly Tyr
225                 230                 235                 240

Phe Gly Glu Val Trp Glu Gly Leu Trp Leu Gly Ser Leu Pro Val Ala
                245                 250                 255

Ile Lys Val Ile Lys Ser Ala Asn Met Lys Leu Thr Asp Leu Ala Lys
                260                 265                 270

Glu Ile Gln Thr Leu Lys Gly Leu Arg His Glu Arg Leu Ile Arg Leu
            275                 280                 285

His Ala Val Cys Ser Gly Gly Glu Pro Val Tyr Ile Val Thr Glu Leu
            290                 295                 300

Met Arg Lys Gly Asn Leu Gln Ala Phe Leu Gly Thr Pro Glu Gly Arg
305                 310                 315                 320

Ala Leu Arg Leu Pro Pro Leu Leu Gly Phe Ala Cys Gln Val Ala Glu
                325                 330                 335

Gly Met Ser Tyr Leu Glu Glu Gln Arg Val Val His Arg Asp Leu Ala
                340                 345                 350

Ala Arg Asn Val Leu Val Asp Asp Gly Leu Ala Cys Lys Val Ala Asp
            355                 360                 365

Phe Gly Leu Ala Arg Leu Leu Lys Asp Asp Ile Tyr Ser Pro Ser Ser
370                 375                 380

Ser Ser Lys Ile Pro Val Lys Trp Thr Ala Pro Glu Ala Ala Asn Tyr
385                 390                 395                 400

Arg Val Phe Ser Gln Lys Ser Asp Val Trp Ser Phe Gly Val Leu Leu
                405                 410                 415

His Glu Val Phe Thr Tyr Gly Gln Cys Pro Tyr Glu Gly Met Thr Asn
            420                 425                 430

His Glu Thr Leu Gln Gln Ile Met Arg Gly Tyr Arg Leu Pro Arg Pro
            435                 440                 445

Ala Ala Cys Pro Ala Glu Val Tyr Val Leu Met Leu Glu Cys Trp Arg
            450                 455                 460

Ser Ser Pro Glu Glu Arg Pro Ser Phe Ala Thr Leu Arg Glu Lys Leu
465                 470                 475                 480
```

His Ala Ile His Arg Cys His Pro
            485

(2) INFORMATION FOR SEQ ID NO: 3:

(i) SEQUENCE CHARACTERISTICS:
        (A) LENGTH:       5 amino acids
        (B) TYPE:         amino acid
        (C) STRANDEDNESS: single
        (D) TOPOLOGY:     linear (ii) MOLECULE TYPE:    peptide (ix) FEATURE:
        (D) OTHER INFORMATION:  "Xaa" in position 3 stands for
            either Glu or Asp.

(xi) SEQUENCE DESCRIPTION: SEQ ID NO: 3:

Phe Gly Xaa Val Trp
1               5

(2) INFORMATION FOR SEQ ID NO: 4:

(i) SEQUENCE CHARACTERISTICS:
        (A) LENGTH:       5 amino acids
        (B) TYPE:         amino acid
        (C) STRANDEDNESS: single
        (D) TOPOLOGY:     linear (ii) MOLECULE TYPE:    peptide (xi) SEQUENCE DESCRIPTION: SEQ ID NO: 4:

Trp Thr Ala Pro Glu
1               5

(2) INFORMATION FOR SEQ ID NO: 5:

(i) SEQUENCE CHARACTERISTICS:
        (A) LENGTH:       21 base pairs
        (B) TYPE:         nucleic acid
        (C) STRANDEDNESS: single
        (D) TOPOLOGY:     linear (ix) FEATURE:
        (D) OTHER INFORMATION:  The letter "N" stands for A, C, G
            or T.
            The letter "R" stands for A or G.
            The letter "Y" stands for C or T.

(xi) SEQUENCE DESCRIPTION: SEQ ID NO: 5:

GGNCARTTYG GNGANGTNTG G                                        21

(2) INFORMATION FOR SEQ ID NO: 6:

(i) SEQUENCE CHARACTERISTICS:
        (A) LENGTH:       24 base pairs
        (B) TYPE:         nucleic acid
        (C) STRANDEDNESS: single
        (D) TOPOLOGY:     linear (ix) FEATURE:
        (D) OTHER INFORMATION:  The letter "N" stands for A, C, G
            or T.
            The letter "Y" stands for C or T.

(xi) SEQUENCE DESCRIPTION: SEQ ID NO: 6:

CAGNGCNGCY TCNGGNGCNG TCCA                                     24

(2) INFORMATION FOR SEQ ID NO: 7:

```
    (i) SEQUENCE CHARACTERISTICS:
        (A) LENGTH:        7 amino acids
        (B) TYPE:          amino acid
        (C) STRANDEDNESS:  single
        (D) TOPOLOGY:      linear (ii) MOLECULE TYPE:    peptide (ix) FEATURE:
        (D) OTHER INFORMATION:   "Xaa" in position 5 stands for
            either Glu or Asp.

(xi) SEQUENCE DESCRIPTION: SEQ ID NO: 7:

Gly Gln Phe Gly Xaa Val Trp
 1               5

(2) INFORMATION FOR SEQ ID NO: 8:

(i) SEQUENCE CHARACTERISTICS:
        (A) LENGTH:        8 amino acids
        (B) TYPE:          amino acid
        (C) STRANDEDNESS:  single
        (D) TOPOLOGY:      linear (ii) MOLECULE TYPE:    peptide (xi) SEQUENCE DESCRIPTION: SEQ ID NO: 8:

Trp Thr Ala Pro Glu Ala Leu Leu
 1               5

(2) INFORMATION FOR SEQ ID NO: 9:

(i) SEQUENCE CHARACTERISTICS:
        (A) LENGTH:        19 base pairs
        (B) TYPE:          nucleic acid
        (C) STRANDEDNESS:  single
        (D) TOPOLOGY:      linear (xi) SEQUENCE DESCRIPTION: SEQ ID NO: 9:

AGTGAGCTTC ATGTTGGCT                                             19

(2) INFORMATION FOR SEQ ID NO: 10:

(i) SEQUENCE CHARACTERISTICS:
        (A) LENGTH:        18 base pairs
        (B) TYPE:          nucleic acid
        (C) STRANDEDNESS:  single
        (D) TOPOLOGY:      linear (xi) SEQUENCE DESCRIPTION: SEQ ID NO: 10:

GGTAGAGGCT GCCATCAG                                              18

(2) INFORMATION FOR SEQ ID NO: 11:

(i) SEQUENCE CHARACTERISTICS:
        (A) LENGTH:        19 base pairs
        (B) TYPE:          nucleic acid
        (C) STRANDEDNESS:  single
        (D) TOPOLOGY:      linear (ix) FEATURE:
        (D) OTHER INFORMATION:   The letter "N" stands for
            deoxythymidylate.

(xi) SEQUENCE DESCRIPTION: SEQ ID NO: 11:

GACGATCGGA ATTCGCGAN                                             19

(2) INFORMATION FOR SEQ ID NO: 12:
```

```
    (i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO: 12:

GACGATCGGA ATTCGCGA                                                       18

(2) INFORMATION FOR SEQ ID NO: 13:

(i) SEQUENCE CHARACTERISTICS:
        (A) LENGTH:       17 base pairs
        (B) TYPE:         nucleic acid
        (C) STRANDEDNESS: single
        (D) TOPOLOGY:     linear (xi) SEQUENCE DESCRIPTION: SEQ ID NO: 13:

CCCAGCCACA GGCCTTC                                                        17

(2) INFORMATION FOR SEQ ID NO: 14:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO: 14:

CCACACCTCC CCAAAGTA                                                       18

(2) INFORMATION FOR SEQ ID NO: 15:

(i) SEQUENCE CHARACTERISTICS:
        (A) LENGTH:       30 base pairs
        (B) TYPE:         nucleic acid
        (C) STRANDEDNESS: single
        (D) TOPOLOGY:     linear (xi) SEQUENCE DESCRIPTION: SEQ ID NO: 15:

TGGGAGCGGC CACACTCCGA ATTCGCCCTT                                          30

(2) INFORMATION FOR SEQ ID NO: 16:

(i) SEQUENCE CHARACTERISTICS:
        (A) LENGTH:       17 base pairs
        (B) TYPE:         nucleic acid
        (C) STRANDEDNESS: single
        (D) TOPOLOGY:     linear (xi) SEQUENCE DESCRIPTION: SEQ ID NO: 16:

GCCTGCGTGC GAAGATG                                                        17

(2) INFORMATION FOR SEQ ID NO: 17:

(i) SEQUENCE CHARACTERISTICS:
        (A) LENGTH:       18 base pairs
        (B) TYPE:         nucleic acid
        (C) STRANDEDNESS: single
        (D) TOPOLOGY:     linear (xi) SEQUENCE DESCRIPTION: SEQ ID NO: 17:

CTTCGAGGGC ACAGAGCC                                                       18

(2) INFORMATION FOR SEQ ID NO: 18:

(i) SEQUENCE CHARACTERISTICS:
```

```
            (A) LENGTH:        21 base pairs
            (B) TYPE:          nucleic acid
            (C) STRANDEDNESS:  single
            (D) TOPOLOGY:      linear (xi) SEQUENCE DESCRIPTION: SEQ ID NO: 18:

ATGGAGCCGT TCCTCAGGAG G                                              21

(2) INFORMATION FOR SEQ ID NO: 19:

(i) SEQUENCE CHARACTERISTICS:
            (A) LENGTH:        21 base pairs
            (B) TYPE:          nucleic acid
            (C) STRANDEDNESS:  single
            (D) TOPOLOGY:      linear (xi) SEQUENCE DESCRIPTION: SEQ ID NO: 19:

TCACCCAGCT TCCTCCCAAG G                                              21

(2) INFORMATION FOR SEQ ID NO: 20:

(i) SEQUENCE CHARACTERISTICS:
            (A) LENGTH:        21 base pairs
            (B) TYPE:          nucleic acid
            (C) STRANDEDNESS:  single
            (D) TOPOLOGY:      linear (xi) SEQUENCE DESCRIPTION: SEQ ID NO: 20:

AGGCCAACTG GAAGCTGATC C                                              21

(2) INFORMATION FOR SEQ ID NO: 21:

(i) SEQUENCE CHARACTERISTICS:
            (A) LENGTH:        20 base pairs
            (B) TYPE:          nucleic acid
            (C) STRANDEDNESS:  single
            (D) TOPOLOGY:      linear (xi) SEQUENCE DESCRIPTION: SEQ ID NO: 21:

GCTGGAGCCC AGAGCGTTGG                                                20

(2) INFORMATION FOR SEQ ID NO: 22:

(i) SEQUENCE CHARACTERISTICS:
            (A) LENGTH:        8 amino acids
            (B) TYPE:          amino acid
            (C) STRANDEDNESS:  single
            (D) TOPOLOGY:      linear (ii) MOLECULE TYPE:        peptide (ix) FEATURE:
            (D) OTHER INFORMATION:  "Xaa" in position 6 stands
                for an unspecified amino acid.

(xi) SEQUENCE DESCRIPTION: SEQ ID NO: 22:

His Arg Asp Leu Arg Xaa Ala Asn
 1               5

(2) INFORMATION FOR SEQ ID NO: 23:

(i) SEQUENCE CHARACTERISTICS:
            (A) LENGTH:        8 amino acids
            (B) TYPE:          amino acid
            (C) STRANDEDNESS:  single
            (D) TOPOLOGY:      linear (ii) MOLECULE TYPE:        peptide
```

```
    (ix) FEATURE:
         (D) OTHER INFORMATION:  "Xaa" in positions 6 stands
             for an unspecified amino acid.

(xi) SEQUENCE DESCRIPTION: SEQ ID NO: 23:

His Arg Asp Leu Ala Xaa Arg Asn
1               5

(2) INFORMATION FOR SEQ ID NO: 24:

(i) SEQUENCE CHARACTERISTICS:
         (A) LENGTH:        21 base pairs
         (B) TYPE:          nucleic acid
         (C) STRANDEDNESS:  single
         (D) TOPOLOGY:      linear (xi) SEQUENCE DESCRIPTION: SEQ ID NO: 24:

TCGCCAAGGA GATCCAGACA C                                            21

(2) INFORMATION FOR SEQ ID NO: 25:

(i) SEQUENCE CHARACTERISTICS:
         (A) LENGTH:        21 base pairs
         (B) TYPE:          nucleic acid
         (C) STRANDEDNESS:  single
         (D) TOPOLOGY:      linear (xi) SEQUENCE DESCRIPTION: SEQ ID NO: 25:

GAAGTCAGCC ACCTTGCAGG C                                            21

(2) INFORMATION FOR SEQ ID NO: 26:

(i) SEQUENCE CHARACTERISTICS:
         (A) LENGTH:        13 base pairs
         (B) TYPE:          nucleic acid
         (C) STRANDEDNESS:  single
         (D) TOPOLOGY:      linear (xi) SEQUENCE DESCRIPTION: SEQ ID NO: 26:

GGATCCCCGG ACC                                                     13

(2) INFORMATION FOR SEQ ID NO: 27:

(i) SEQUENCE CHARACTERISTICS:
         (A) LENGTH:        10 amino acids
         (B) TYPE:          amino acid
         (C) STRANDEDNESS:  single
         (D) TOPOLOGY:      linear (ii) MOLECULE TYPE:     peptide (xi) SEQUENCE DESCRIPTION: SEQ ID NO: 27:

Met Arg Gly Ser His His His His His His
1               5                   10

(2) INFORMATION FOR SEQ ID NO: 28:

(i) SEQUENCE CHARACTERISTICS:
         (A) LENGTH:        30 base pairs
         (B) TYPE:          nucleic acid
         (C) STRANDEDNESS:  single
         (D) TOPOLOGY:      linear (xi) SEQUENCE DESCRIPTION: SEQ ID NO: 28:

ATGAGAGGAT CGCATCACCA TCACCATCAC                                   30
```